US010098969B2

(12) United States Patent
Darvish et al.

(10) Patent No.: US 10,098,969 B2
(45) Date of Patent: Oct. 16, 2018

(54) METHODS AND COMPOSITIONS FOR INCREASING SIALIC ACID PRODUCTION AND TREATING SIALIC RELATED DISEASE CONDITIONS

(71) Applicant: HIBM Research Group, Inc., Chatsworth, CA (US)

(72) Inventors: Daniel Darvish, Sherman Oaks, CA (US); Yadira Valles-Ayoub, Woodland Hills, CA (US)

(*) Notice: Subject to any disclaimer, the term of this patent is extended or adjusted under 35 U.S.C. 154(b) by 0 days.

(21) Appl. No.: 14/285,602

(22) Filed: May 22, 2014

(65) Prior Publication Data
US 2014/0275230 A1 Sep. 18, 2014

Related U.S. Application Data

(63) Continuation of application No. 13/364,181, filed on Feb. 1, 2012, now abandoned.

(60) Provisional application No. 61/438,585, filed on Feb. 1, 2011.

(51) Int. Cl.
*A61K 48/00* (2006.01)
*A61K 38/52* (2006.01)
*A61M 5/42* (2006.01)

(52) U.S. Cl.
CPC ............ *A61K 48/005* (2013.01); *A61K 38/52* (2013.01); *A61K 48/0083* (2013.01); *A61M 5/425* (2013.01)

(58) Field of Classification Search
None
See application file for complete search history.

(56) References Cited

U.S. PATENT DOCUMENTS

| 2006/0218670 | A1 | 9/2006 | Joshi et al. |
| 2007/0073264 | A1 | 3/2007 | Stedman et al. |
| 2009/0298112 | A1 | 12/2009 | Darvish et al. |
| 2010/0184158 | A1 | 7/2010 | Williams |
| 2011/0027373 | A1 | 2/2011 | Maples et al. |

FOREIGN PATENT DOCUMENTS

| JP | 2010519184 A | 6/2010 |
| WO | 2004062368 A1 | 7/2004 |
| WO | 2008097623 A2 | 8/2008 |
| WO | 2008124934 A1 | 10/2008 |
| WO | 2010030666 A2 | 3/2010 |

OTHER PUBLICATIONS

Sun et al., Correction of Glycogen Storage Disease Type II by an Adeno-associated Virus Vector Containing a Muscle-Specific Promoter. Mol Ther. Jun. 2005;11(6):889-898.
Tajima et al., Distal Myopathy with Rimmed Vacuoles: Impaired O-Glycan Formation in Muscular Glycoproteins. Am J Pathol. Apr. 2005;166(4):1121-1130.
Talbot et al., Desmin-regulated Lentiviral Vectors for Skeletal Muscle Gene Transfer. Mol Ther. Mar. 2010;18(3):601-608.
Tangvoranuntakul et al., Human uptake and incorporation of an immunogenic nonhuman dietary sialic acid. Proc Natl Acad Sci USA. Oct. 14, 2003;100(21):12045-12050.
Toromanoff et al., Safety and Efficacy of Regional Intravenous (RI) Versus Intramuscular (IM) Delivery of rAAV1 and rAAV8 to Nonhuman Primate Skeletal Muscle. Mol Ther. Jul. 2008;16(7):1291-1299.
Toumi et al., Rapid Intravascular Injection into Limb Skeletal Muscle: A Damage Assessment Study. Mol Ther. Jan. 2006;13(1):229-236.
Urthaler et al., Automated alkaline lysis for industrial scale cGMP production of pharmaceutical grade plasmid-DNA. J Biotechnol. Jan. 30, 2007;128(1):132-149.
Varki, Multiple changes in sialic acid biology during human evolution. Glycoconj J. Apr. 2009;26(3):231-245.
Vigen et al., Magnetic Resonance Imaging-Monitored Plasmid DNA Delivery in Primate Limb Muscle. Hum Gene Ther. Mar. 2007;18(3):257-268.
Vlassakov and Bhavani, The forearm tourniquet Bier block. Logic and authority versus science and experience. Minerva Anestesiol. Feb. 2010;76(2):91-92.
Voss, Production of plasmid DNA for pharmaceutical use. Biotechnol Annu Rev. 2007;13:201-222.
Walther et al., Stability analysis for long-term storage of naked DNA: impact on nonviral in vivo gene transfer. Anal Biochem. Jul. 15, 2003;318(2):230-235.
Wang et al., Construction and analysis of compact muscle-specific promoters for AAV vectors. Gene Ther. Nov. 2008;15(22):1489-1499.
Wang et al., Roles for UDP-GlcNAc 2-Epimerase/ManNAc 6-Kinase outside of Sialic Acid Biosynthesis: modulation of sialyltransferase and BiP expression, GM3 and GD3 biosynthesis, proliferation, and apoptosis, and ERK1/2 phosphorylation. J Biol Chem. Sep. 15, 2006;281(37):27016-27028.
Warren, The Thiobarbituric Acid Assay of Sialic Acids. J Biol Chem. Aug. 1959;234(8):1971-1975.

(Continued)

Primary Examiner — Robert M Kelly

(57) ABSTRACT

Disclosed herein are methods of expressing UDP-GlcNAc 2-Epimerase/ManNAc Kinase enzyme (GNE) peptide in a cell of a subject comprising: delivering into the cell of the subject an isolated nucleic acid expression construct that comprises a promoter operatively linked to a nucleic acid sequence encoding a GNE peptide or a therapeutically active fragment thereof, wherein the GNE peptide has the amino acid sequence of SEQ ID NO: 3, wherein upon the delivering into the cell of the subject, the nucleic acid expression construct initiates expression of the GNE peptide or a therapeutically active fragment thereof. Also disclosed are methods of producing a GNE peptide in a cell comprising infecting the cell with an isolated nucleic acid construct that comprises a promoter operatively linked to a nucleic acid sequence encoding a GNE peptide or a therapeutically active fragment thereof, wherein the GNE peptide has the amino acid sequence of SEQ ID NO: 3.

3 Claims, 15 Drawing Sheets
Specification includes a Sequence Listing.

(56) References Cited

OTHER PUBLICATIONS

Wells, Opening the Floodgates: Clinically Applicable Hydrodynamic Delivery of Plasmid DNA to Skeletal Muscle. Mol Ther. Aug. 2004;10(2):207-208.
Williams et al., Plasmid DNA vaccine vector design: impact on efficacy, safety and upstream production. Biotechnol Adv. Jul.-Aug. 2009;27(4):353-370.
Wolff and Budker, The Mechanism of Naked DNA Uptake and Expression. Adv Genet. 2005;54:3-20.
Wolff et al., Non-viral approaches for gene transfer. Acta Myol. Dec. 2005;24(3):202-208.
Yuasa et al., Adeno-associated virus vector-mediated gene transfer into dystrophin-deficient skeletal muscles evokes enhanced immune response against the transgene product. Gene Ther. Dec. 2002;9(23):1576-1588.
Yuasa et al., Injection of a recombinant AAV serotype 2 into canine skeletal muscles evokes strong immune responses against transgene products. Gene Ther. Sep. 2007;14(17):1249-1260.
Zhang et al., Functional Efficacy of Dystrophin Expression from Plasmids Delivered to mdx Mice by Hydrodynamic Limb Vein Injection. Hum Gene Ther. Feb. 2010;21(2):221-237.
Amouri et al., Allelic heterogeneity of GNE gene mutation in two Tunisian families with autosomal recessive inclusion body myopathy. Neuromuscul Disord. May 2005;15(5):361-363 (abstract only).
Bork et al. Enhanced sialylation of EPO by overexpression of UDP-GlcNAc 2-epimerase/ManAc kinase containing a sialuria mutation in CHO cells. FEBS Lett. Sep 4, 2007;581(22):4195-4198.
Extended European Search Report and Written Opinion issued in EP 12742231 dated Jun. 26, 2015.
International Search Report and Written Opinion issued in PCT/US2012/023536 dated Jun. 8, 2012.
Office Action issued by the JPO in Japanese application No. 2013-552609 dated Dec. 1, 2015.
Hong and Stanley, Lec3 Chinese Hamster Ovary Mutants Lack UDP-N-acetylglucosamine 2-Epimerase Activity Because of Mutations in the Epimerase Domain of the Gne Gene. J Biol Chem. Dec. 26, 2003;278(52):53045-53054.
Valles-Ayoub et al., Development and Functional Analysis of Wildtype and R266Q GNE Expression Plasmids. Mol Ther. May 2009;17(Suppl 1):S333.
Yang et al., Cellular uptake of self-assembled cationic peptide-DNA complexes: Multifunctional role of the enhancer chloroquine. J Control Release. Apr. 17, 2009;135(2):159-165.
Jay et al., Preclinical Assessment of wt GNE Gene Plasmid for Management of Hereditary Inclusion Body Myopathy 2 (HIBM2). Gene Regul Syst Bio. Jun. 20, 2008;2:243-252.
Al-Dosari et al., Hydrodynamic Delivery. Adv Genet. 2005;54:65-82.
Amsili et al., Characterization of hereditary inclusion body myopathy myoblasts: possible primary impairment of apoptotic events. Cell Death Differ. Nov. 2007;14(11):1916-1924.
Amsili et al., UDP-N-acetylglucosamine 2-epimerase/N-acetylmannosamine kinase (GNE) binds to alpha-actinin 1: novel pathways in skeletal muscle? PLoS One. Jun. 18, 2008;3(6):e2477.
Arruda et al., Regional intravascular delivery of AAV-2-F.IX to skeletal muscle achieves long-term correction of hemophilia B in a large animal model. Blood. May 1, 2005;105(9):3458-3464.
Blain et al., Strong Muscle-Specific Regulatory Cassettes Based on Multiple Copies of the Human Slow Troponin I Gene Upstream Enhancer. Hum Gene Ther Jan. 2010;21(1):127-134.
Braun, Muscular Gene Transfer Using Nonviral Vectors. Curr Gene Ther. Oct. 2008;8(5):391-405.
Broccolini et al., Alpha-Dystroglycan does not play a major pathogenic role in autosomal recessive hereditary inclusion-body myopathy. Neuromuscul Disord. Feb. 2005;15(2):177-184.
Danko et al., Dystrophin expression improves myofiber survival in mdx muscle following intramuscular plasmid DNA injection. Hum Mol Genet. Dec. 1993;2(12):2055-2061.

Danko et al., High Expression of Naked Plasmid DNA in Muscles of Young Rodents. Hum Mol Genet. Sep. 1997;6(9):1435-1443.
dos Reis, Anestesia Regional Intravenosa—Primeiro Centenário (1908-2008). Início, Desenvolvimento e Estado Atual [Intravenous Regional Anesthesia—First Century (1908-2008). Beggining, Development, and Current Status]. Rev Bras Anestesiol May-Jun. 2008;58(3):299-321 (includes Engl translation).
Duan, Myodys, A full-length dystrophin plasmid vector for Duchenne and Becker muscular dystrophy gene therapy. Curr Opin Mol Ther. Feb. 2008;10(1):86-94.
Fabre et al., Comparison of promoter region constructs for in vivo intramuscular expression. J Gene Med. May 2006;8(5):636-645.
Fan et al., Safety and Feasibility of High-pressure Transvenous Limb Perfusion With 0.9% Saline in Human Muscular Dystrophy. Molecular Therapy Feb. 2012;20(2):456-461.
Galeano et al., Mutation in the key enzyme of sialic acid biosynthesis causes severe glomerular proteinuria and is rescued by N-acetylmannosamine. J Clin Invest. Jun. 2007;117(6):1585-1594.
Glover et al., Towards safe, non-viral therapeutic gene expression in humans. Nat Rev Genet. Apr. 2005;6(4)299-310.
Gonin et al., Femoral intra-arterial injection: a tool to deliver and assess recombinant AAV constructs in rodents whole hind limb. J Gene Med. Jun. 2005;7(6):782-791.
Hagstrom et al., A Facile Nonviral Method for Delivering Genes and siRNAs to Skeletal Muscle of Mammalian Limbs. Mol Ther. Aug. 2004;10(2):386-398.
Haurigot et al., Safety of AAV Factor IX Peripheral Transvenular Gene Delivery to Muscle in Hemophilia B Dogs. Mol Ther. Jul. 2010;18(7):1318-1329.
Hauser et al., Analysis of Muscle Creatine Kinase Regulatory Elements in Recombinant Adenoviral Vectors. Mol Ther. Jul. 2000;2(1):16-25.
Hedlund et al., Evidence for a human-specific mechanism for diet and antibody-mediated inflammation in carcinoma progression. Proc Natl Mad Sci U S A. Dec. 2, 2008;105(48):18936-18941.
Hegge et al., Evaluation of Hydrodynamic Limb Vein Injections in Nonhuman Primates. Hum Gene Ther. Jul. 2010;21(7):829-842.
Herweijer and Wolff, Gene therapy progress and prospects: Hydrodynamic gene delivery. Gene Ther. Jan. 2007;14(2):99-107.
Hinderlich et al., The homozygous M712T mutation of UDP-N-acetylglucosamine 2-epimerase/N-acetylmannosamine kinase results in reduced enzyme activities but not in altered overall cellular sialylation in hereditary inclusion body myopathy. FEBS Lett. May 21, 2004;566(1-3):105-109.
Huizing et al., Hypoglycosylation of alpha-dystroglycan in patients with hereditary IBM due to GNE mutations. Mol Genet Metab. Mar. 2004;81(3):196-202.
Jiao et al., Direct Gene Transfer into Nonhuman Primate Myofibers In Vivo. Hum Gene Ther. Feb. 1992;3(1):21-33.
Kontou et al., The key enzyme of sialic acid biosynthesis (GNE) promotes neurite outgrowth of PC12 cells. Neuroreport. Aug. 6, 2008;19(12):1239-1242.
Kontou et al., Beyond glycosylation: sialic acid precursors act as signaling molecules and are involved in cellular control of differentiation of PC12 cells. Biol Chem. Jul. 2009;390(7):575-579.
Krause et al., Localization of UDP-GlcNAc 2-epimerase/ManAc kinase (GNE) in the Golgi complex and the nucleus of mammalian cells. Exp Cell Res. Apr. 1, 2005;304(2):365-79.
Kroon and Thompson, Isolated Limb Infusion: A Review. J Surg Oncol. Aug. 1, 2009;100(2):169-177.
Li et al. Synthetic muscle promoters: activities exceeding naturally occurring regulatory sequences. Nat Biotechnol. Mar. 1999;17(3)241-245.
Liu et al., Mechanism of naked DNA clearance after intravenous injection. J Gene Med. Jul. 2007;9(7):613-619.
Lofling et al., A dietary non-human sialic acid may facilitate hemolytic-uremic syndrome. Kidney Int. Jul. 2009;76(2):140-144.
Lu et al., Non-viral gene delivery in skeletal muscle: a protein factory. Gene Ther. Jan. 2003;10(2):131-142.
Malicdan et al., Prophylactic treatment with sialic acid metabolites precludes the development of the myopathic phenotype in the DMRV-hIBM mouse model. Nat Med. Jun. 2009;15(6):690-695.

(56) References Cited

OTHER PUBLICATIONS

Mingozzi et al., AAV-1-mediated gene transfer to skeletal muscle in humans results in dose-dependent activation of capsid-specific T cells. Blood. Sep. 3, 2009;114(10):2077-2086.

Nemunaitis et al., Hereditary inclusion body myopathy: single patient response to GNE gene Lipoplex therapy. J Gene Med. May 2010;12(5):403-412.

Noguchi et al. Reduction of UDP-N-acetylglucosamine 2-Epimerase/N-Acetylmannosamine Kinase Activity and Sialylation in Distal Myopathy with Rimmed Vacuoles. J Biol Chem. Mar. 19, 2004;279(12):11402-11407.

Pacak et al., Tissue specific promoters improve specificity of AAV9 mediated transgene expression following intra-vascular gene delivery in neonatal mice. Genet Vaccines Ther. Sep. 23, 2008;6:13.

Paccalet et al., Ganglioside GM3 Levels Are Altered in a Mouse Model of HIBM: GM3 as a Cellular Marker of the Disease. PLoS One. Apr. 7, 2010;5(4):e10055.

Penner et al., Influence of UDP-GlcNAc 2-Epimerase/ManNAc Kinase Mutant Proteins on Hereditary Inclusion Body Myopathy. Biochemistry. Mar. 7, 2006;45(9):2968-2977.

Phadke et al., Safety and in vivo Expression of a GNE-Transgene: A Novel Treatment Approach for Hereditary Inclusion Body Myopathy-2. Gene Regul Syst Bio. May 2009 8;3:89-101.

Ratanamart and Shaw, Plasmid-Mediated Muscle-Targeted Gene Therapy for Circulating Therapeutic Protein Replacement: A Tale of the Tortoise and the Hare? Curr Gene Ther. Feb. 2006;6(1):93-110.

Ricci et al., NCAM is hyposialylated in hereditary inclusion body myopathy due to GNE mutations. Neurology. Mar. 14, 2006;66(5):755-758.

Romero et al., Phase I Study of Dystrophin Plasmid-Based Gene Therapy in Duchenne/Becker Muscular Dystrophy. Hum Gene Ther. Nov. 2004;15(11):1065-1076.

Saito et al., A Japanese patient with distal myopathy with rimmed vacuoles: missense mutations in the epimerase domain of the UDP-N-acetylglucosamine 2-epimerase/N-acetylmannosamine kinase (GNE) gene accompanied by hyposialylation of skeletal muscle glycoproteins. Neuromuscul Disord. Feb. 2004;14(2):158-161.

Salama et al., No overall hyposialylation in hereditary inclusion body myopathy myoblasts carrying the homozygous M712T GNE mutation. Biochem Biophys Res Commun. Mar. 4, 2005;328(1):221-226.

Salva et al., Design of Tissue-specific Regulatory Cassettes for High-level rAAV-mediated Expression in Skeletal and Cardiac Muscle. Mol Ther. Feb. 2007;15(2):320-329.

Sebestyen et al., Progress toward a nonviral gene therapy protocol for the treatment of anemia. Hum Gene Ther. Mar. 2007;18(3):269-285.

Sparks et al., Intravenous immune globulin in hereditary inclusion body myopathy: a pilot study. BMC Neurol. Jan. 29, 2007;7:3.

Su et al., Uniform Scale-Independent Gene Transfer to Striated Muscle After Transvenular Extravasation of Vector. Circulation. Sep. 20, 2005;112(12):1780-1788.

Figure 2

```
   1 ccgcctaatg agcgggcttt tttttcttag ggtgcaaaag gagagcctgt
  51 aagcgggcac tcttccgtgg tctggtggat aaattcgcaa gggtatcatg
 101 gcggacgacc ggggttcgag ccccgtatcc ggccgtccgc cgtgatccat
 151 gcggttaccg cccgcgtgtc gaacccaggt gtgcgacgtc agacaacggg
 201 ggagtgctcc ttttggcttc cttccctac cggtctgcct cgcgcgtttc
 251 ggtgatgacg gtgaaaacct ctgacacatg cagctcccgg agacggtcac
 301 agcttgtctg taagcggatg ccgggagcag acaagcccgt cagggcgcgt
 351 cagcgggtgt tggcgggtgt cggggcgcag ccatgaccca gtcacgtagc
 401 gatagcggag tgtatactgg cttaactatg cggcatcaga gcagattgta
 451 ctgagagtgc accatatgcg gtgtgaaata ccgcacagat gcgtaaggag
 501 aaaataccgc atcaggcgct cttccgcttc ctcgctcact gactcgctgc
 551 gctcggtcgt tcggctgcgg cgagcggtat cagctcactc aaaggcggta
 601 atacggttat ccacagaatc aggggataac gcaggaaaga acatgtgagc
 651 aaaaggccag caaaaggcca ggaaccgtaa aaaggccgcg ttgctggcgt
 701 ttttccatag gctccgcccc cctgacgagc atcacaaaaa tcgacgctca
 751 agtcagaggt ggcgaaaccc gacaggacta taaagatacc aggcgtttcc
 801 ccctggaagc tccctcgtgc gctctcctgt tccgaccctg ccgcttaccg
 851 gatacctgtc cgcctttctc ccttcgggaa gcgtggcgct ttctcatagc
 901 tcacgctgta ggtatctcag ttcggtgtag gtcgttcgct ccaagctggg
 951 ctgtgtgcac gaaccccccg ttcagcccga ccgctgcgcc ttatccggta
1001 actatcgtct tgagtccaac ccggtaagac acgacttatc gccactggca
1051 gcagccactg gtaacaggat tagcagagcg aggtatgtag gcggtgctac
1101 agagttcttg aagtggtggc ctaactacgg ctacactaga agaacagtat
1151 ttggtatctg cgctctgctg aagccagtta ccttcggaaa aagagttggt
1201 agctcttgat ccggcaaaca aaccaccgct ggtagcggtg gtttttttgt
1251 ttgcaagcag cagattacgc gcagaaaaaa aggatctcaa gaagatcctt
1301 tgatcttttc tacggggtct gacgctcagt ggaacgaaaa ctcacgttaa
1351 gggattttgg tcatgagatt atcaaaaagg atcttcacct agatcctttt
1401 aaattaaaaa tgaagtttta aatcaatcta agtatatat gagtaaactt
1451 ggtctgacag ttaccaatgc ttaatcagtg aggcacctat ctcagcgatc
1501 tgtctatttc gttcatccat agttgcctga ctcctgcaaa ccacgttgtg
1551 gtagaattgg taaagagagt cgtgtaaaat atcgagttcg cacatcttgt
1601 tgtctgatta ttgattttg gcgaaaccat ttgatcatat gacaagatgt
1651 gtatctacct taacttaatg attttgataa aaatcattag gtaccctga
1701 tcactgtgga atgtgtgtca gttagggtgt ggaaagtccc caggctcccc
1751 agcaggcaga agtatgcaaa gcatgcatct caattagtca gcaaccaggt
1801 gtggaaagtc cccaggctcc ccagcaggca gaagtatgca aagcatgcat
1851 ctcaattagt cagcaaccat agtcccgccc ctaactccgc ccatcccgcc
1901 cctaactccg cccagttacg ggtcattag ttcatagccc atatatggag
1951 ttccgcgtta cataacttac ggtaaatggc ccgcctggct gaccgcccaa
2001 cgacccccgc ccattgacgt caataatgac gtatgttccc atagtaacgc
2051 caatagggac tttccattga cgtcaatggg tggagtattt acggtaaact
2101 gcccacttgg cagtacatca agtgtatcat atgccaagta cgccccctat
2151 tgacgtcaat gacggtaaat ggcccgcctg gcattatgcc cagtacatga
2201 ccttatggga cttttcctact tggcagtaca tctacgtatt agtcatcgct
2251 attaccatgg tgatgcggtt ttggcagtac atcaatgggc gtggatagcg
2301 gtttgactca cggggatttc caagtctcca ccccattgac gtcaatggga
2351 gtttgttttg gcaccaaaat caacgggact ttccaaaatg tcgtaacaac
2401 tccgccccat tgacgcaaat gggcggtagg cgtgtacggt gggaggtcta
2451 tataagcaga gctcgtttag tgaaccgtca gatcgcctgg agacgccatc
2501 cacgctgttt tgacctccat agaagacacc gggaccgatc cagcctccgc
2551 ggctcgcatc tctccttcac gcgcccgccg cctacctga ggccgccatc
2601 cacgccggtt gagtcgcgtt ctgccgcctc ccgcctgtgg tgcctcctga
```

Figure 2 (cont'd)

```
2651 actgcgtccg ccgtctaggt aagtttaaag ctcaggtcga gaccgggcct
2701 ttgtccggcg ctcccttgga gcctacctag actcagccgg ctctccacgc
2751 tttgcctgac cctgcttgct caactctagt tctctcgtta acttaatgag
2801 acagatagaa actggtcttg tagaaacaga gtagtcgcct gcttttctgc
2851 caggtgctga cttctctccc ctgggctttt ttcttttttct caggttgaaa
2901 agaagaagac gaagaagacg aagaagacaa accgtcgtcg acatggagaa
2951 gaatggaaat aaccgaaagc tgcgggtttg tgttgctact tgtaaccgtg
3001 cagattattc taaacttgcc ccgatcatgt ttggcattaa aaccgaacct
3051 gagttctttg aacttgatgt tgtggtactt ggctctcacc tgatagatga
3101 ctatggaaat acatatcgaa tgattgaaca agatgacttt gacattaaca
3151 ccaggctaca cacaattgtg aggggagaag atgaggcagc catggtggag
3201 tcagtaggcc tggccctagt gaagctgcca gatgtcctta atcgcctgaa
3251 gcctgatatc atgattgttc atggagacag gtttgatgcc ctggctctgg
3301 ccacatctgc tgccttgatg aacatccgaa tccttcacat tgaaggtggg
3351 gaagtcagtg ggaccattga tgactctatc agacatgcca taacaaaact
3401 ggctcattat catgtgtgct gcaccgcag tgcagagcag cacctgatat
3451 ccatgtgtga ggaccatgat cgcatccttt tggcaggctg cccttcctat
3501 gacaaacttc tctcagccaa gaacaaagac tacatgagca tcattcgcat
3551 gtggctaggt gatgatgtaa aatctaaaga ttacattgtt gcactacagc
3601 accctgtgac cactgacatt aagcattcca taaaaatgtt tgaattaaca
3651 ttggatgcac ttatctcatt taacaagcgg accctagtcc tgtttccaaa
3701 tattgacgca gggagcaaag agatggttcg agtgatgcgg aagaagggca
3751 ttgagcatca tcccaacttt cgtgcagtta aacacgtccc atttgaccag
3801 tttatacagt tggttgccca tgctggctgt atgattggga acagcagctg
3851 tggggttcga gaagttggag cttttggaac acctgtgatc aacctgggaa
3901 cacgtcagat tggaagagaa acaggggaga atgttcttca tgtccgggat
3951 gctgacaccc aagacaaaat attgcaagca ctgcaccttc agtttggtaa
4001 acagtaccct tgttcaaaga tatatgggga tggaaatgct gttccaagga
4051 ttttgaagtt tctcaaatct atcgatcttc aagagccact gcaaaagaaa
4101 ttctgctttc ctcctgtgaa ggagaatatc tctcaagata ttgaccatat
4151 tcttgaaact ctaagtgcct tggccgttga tcttggcggg acgaacctcc
4201 gagttgcaat agtcagcatg aagggtgaaa tagttaagaa gtatactcag
4251 ttcaatccta aaacctatga agagaggatt aatttaatcc tacagatgtg
4301 tgtggaagct gcagcagaag ctgtaaaact gaactgcaga attttgggag
4351 taggcatttc cacaggtggc cgtgtaaatc ctcgggaagg aattgtgctg
4401 cattcaacca aactgatcca agagtggaac tctgtggacc ttaggacccc
4451 cctttctgac actttgcatc tccctgtgtg ggtagacaat gatggcaact
4501 gtgctgccct ggcggaaagg aaatttggcc aaggaaaggg actggaaaac
4551 tttgttacac ttatcacagg cacaggaatc ggtggtggaa ttatccatca
4601 gcatgaattg atccacggaa gctccttctg tgctgcagaa ctgggccacc
4651 ttgttgtgtc tctggatggg cctgattgtt cctgtggaag ccatgggtgc
4701 attgaagcat acgcctctgg aatggccttg cagagggagg caaaaaagct
4751 ccatgatgag gacctgctct tggtggaagg gatgtcagtg ccaaaagatg
4801 aggctgtggg tgcgctccat ctcatccaag ctgcgaaact tggcaatgcg
4851 aaggcccaga gcatcctaag aacagctgga acagctttgg gtcttgggt
4901 tgtgaacatc ctccatacca tgaatccctc ccttgtgatc ctctccggag
4951 tcctggccag tcactatatc cacattgtca aagacgtcat tcgccagcag
5001 gccttgtcct ccgtgcagga cgtggatgtg gtggtttcgg atttggttga
5051 ccccgccctg ctgggtgctg ccagcatggt tctggactac acaacacgca
5101 ggatctacta gtaagatctt tttccctctg ccaaaaatta tggggacatc
5151 atgaagcccc ttgagcatct gacttctggc taataaagga aatttatttt
5201 cattgcaata gtgtgttgga attttttgtg tctctcactc ggaaggacat
5251 aagggcggcc gctagc
```

Figure 4

```
   1 tggccattgc atacgttgta tccatatcat aatatgtaca tttatattgg
  51 ctcatgtcca acattaccgc catgttgaca ttgattattg actagttatt
 101 aatagtaatc aattacgggg tcattagttc atagcccata tatggagttc
 151 cgcgttacat aacttacggt aaatggcccg cctggctgac cgcccaacga
 201 cccccgccca ttgacgtcaa taatgacgta tgttcccata gtaacgccaa
 251 tagggacttt ccattgacgt caatgggtgg agtatttacg gtaaactgcc
 301 cacttggcag tacatcaagt gtatcatatg ccaagtacgc ccectattga
 351 cgtcaatgac ggtaaatggc ccgcctggca ttatgcccag tacatgacct
 401 tatgggactt tcctacttgg cagtacatct acgtattagt catcgctatt
 451 accatggtga tgcggttttg gcagtacatc aatgggcgtg gatagcggtt
 501 tgactcacgg ggatttccaa gtctccaccc cattgacgtc aatgggagtt
 551 tgttttggca ccaaaatcaa cgggactttc caaaatgtcg taacaactcc
 601 gccccattga cgcaaatggg cggtaggcgt gtacggtggg aggtctatat
 651 aagcagagct cgtttagtga accgtcagat cgcctggaga cgccatccac
 701 gctgttttga cctccataga agacaccggg accgatccag cctccgcggc
 751 cgggaacggt gcattggaac gcggattccc cgtgccaaga gtgacgtaag
 801 taccgcctat agactctata ggcacaccec tttggctctt atgcatgcta
 851 tactgttttt ggcttgggggc ctatacaccc ccgcttcctt atgctatagg
 901 tgatggtata gcttagccta taggtgtggg ttattgacca ttattgacca
 951 ctccaacggt ggagggcagt gtagtctgag cagtactcgt tgctgccgcg
1001 cgcgccacca gacataatag ctgacagact aacagactgt tcctttccat
1051 gggtcttttc tgcagtcacc gtcgtcgacg gtatcgataa gcttgatatc
1101 gaattcatgg agaagaatgg aaataaccga aagctgcggg tttgtgttgc
1151 tacttgtaac cgtgcagatt attctaaact tgccccgatc atgtttggca
1201 ttaaaaccga acctgagttc tttgaacttg atgttgtggt acttggctct
1251 cacctgatag atgactatgg aaatacatat cgaatgattg aacaagatga
1301 ctttgacatt aacaccaggc tacacacaat tgtgagggga gaagatgagg
1351 cagccatggt ggagtcagta ggcctggccc tagtgaagct gccagatgtc
1401 cttaatcgcc tgaagcctga tatcatgatt gttcatggag acaggtttga
1451 tgccctggct ctggccacat ctgctgcctt gatgaacatc cgaatccttc
1501 acattgaagg tggggaagtc agtgggacca ttgatgactc tatcagacat
1551 gccataacaa aactggctca ttatcatgtg tgctgcaccc gcagtgcaga
1601 gcagcacctg atatccatgt gtgaggacca tgatccgcatc cttttggcag
1651 gctgcccttc ctatgacaaa cttctctcag ccaagaacaa agactacatg
1701 agcatcattc gcatgtggct aggtgatgat gtaaaatcta aagattacat
1751 tgttgcacta cagcaccctg tgaccactga cattaagcat tccataaaaa
1801 tgtttgaatt aacattggat gcacttatct catttaacaa gcggaccta
1851 gtcctgtttc caaatattga cgcagggagc aaagagatgg ttcgagtgat
1901 gcggaagaag ggcattgagc atcatcccaa ctttcgtgca gttaaacacg
1951 tcccatttga ccagtttata cagttggttg cccatgctgg ctgtatgatt
2001 gggaacagca gctgtgggt tcgagaagtt ggagcttttg aacacctgt
2051 gatcaacctg gaacacgtc agattggaag agaaacaggg gagaatgttc
2101 ttcatgtccg ggatgctgac acccaagaca aatattgca agcactgcac
2151 cttcagtttg gtaaacagta ccettgttca aagatatatg gggatggaaa
2201 tgctgttcca aggattttga agtttctcaa atctatcgat cttcaagagc
2251 cactgcaaaa gaaattctgc tttcctcctg tgaaggagaa tatctctcaa
2301 gatattgacc atattcttga aactctaagt gccttggccg ttgatcttgg
2351 cgggacgaac ctccgagttg caatagtcag catgaagggt gaaatagtta
2401 agaagtatac tcagttcaat cctaaaaacct atgaagagag gattaattta
2451 atcctacaga tgtgtgtgga agctgcagca gaagctgtaa aactgaactg
2501 cagaattttg ggagtaggca tttccacagg tgccgtgta aatcctcggg
2551 aaggaattgt gctgcattca accaaactga tccaagagtg gaactctgtg
2601 gaccttagga cccccctttc tgacactttg catctccctg tgtgggtaga
```

Figure 4 (cont'd)

```
2651 caatgatggc aactgtgctg ccctggcgga aaggaaattt ggccaaggaa
2701 agggactgga aaactttgtt acacttatca caggcacagg aatcggtggt
2751 ggaattatcc atcagcatga attgatccac ggaagctcct tctgtgctgc
2801 agaactgggc caccttgttg tgtctctgga tgggcctgat tgttcctgtg
2851 gaagccatgg gtgcattgaa gcatacgcct ctggaatggc cttgcagagg
2901 gaggcaaaaa agctccatga tgaggacctg ctcttggtgg aagggatgtc
2951 agtgccaaaa gatgaggctg tgggtgcgct ccatctcatc caagctgcga
3001 aacttggcaa tgcgaaggcc cagagcatcc taagaacagc tggaacagct
3051 ttgggtcttg gggttgtgaa catcctccat accatgaatc cctcccttgt
3101 gatcctctcc ggagtcctgg ccagtcacta tatccacatt gtcaaagacg
3151 tcattcgcca gcaggccttg tcctccgtgc aggacgtgga tgtggtggtt
3201 tcggatttgg ttgaccccgc cctgctgggt gctgccagca tggttctgga
3251 ctacacaaca cgcaggatct actaggatcc agatcttttt ccctctgcca
3301 aaaattatgg ggacatcatg aagcccttg agcatctgac ttctggctaa
3351 taaaggaaat ttattttcat tgcaatagtg tgttggaatt ttttgtgtct
3401 ctcactcgga aggacatatg ggagggcaaa tcatttaaaa catcagaatg
3451 agtatttggt ttagagtttg gcaacatatg cccattcttc cgcttcctcg
3501 ctcactgact cgctgcgctc ggtcgttcgg ctgcggcgag cggtatcagc
3551 tcactcaaag gcggtaatac ggttatccac agaatcaggg gataacgcag
3601 gaaagaacat gtgagcaaaa ggccagcaaa aggccaggaa ccgtaaaaag
3651 gccgcgttgc tggcgttttt ccataggctc cgcccccctg acgagcatca
3701 caaaaatcga cgctcaagtc agaggtggcg aaacccgaca ggactataaa
3751 gataccaggc gtttccccct ggaagctccc tcgtgcgctc tcctgttccg
3801 accctgccgc ttaccggata cctgtccgcc tttctccctt cgggaagcgt
3851 ggcgctttct catagctcac gctgtaggta tctcagttcg gtgtaggtcg
3901 ttcgctccaa gctgggctgt gtgcacgaac cccccgttca gcccgaccgc
3951 tgcgccttat ccggtaacta tcgtcttgag tccaacccgg taagacacga
4001 cttatcgcca ctggcagcag ccactggtaa caggattagc agagcgaggt
4051 atgtaggcgg tgctacagag ttcttgaagt ggtggcctaa ctacggctac
4101 actagaagaa cagtatttgg tatctgcgct ctgctgaagc cagttacctt
4151 cggaaaaaga gttggtagct cttgatccgg caaacaaacc accgctggta
4201 gcggtggttt ttttgtttgc aagcagcaga ttacgcgcag aaaaaaagga
4251 tctcaagaag atcctttgat cttttctacg gggtctgacg ctcagtggaa
4301 cgaaaactca cgttaaggga ttttggtcat gagattatca aaaaggatct
4351 tcacctagat ccttttaaat taaaaatgaa gttttaaatc aatctaaagt
4401 atatatgagt aaacttggtc tgacagttac caatgcttaa tcagtgaggc
4451 acctatctca gcgatctgtc tatttcgttc atccatagtt gcctgactcg
4501 ggggggggg gcgctgaggt ctgcctcgtg aagaaggtgt tgctgactca
4551 taccaggcct gaatcgcccc atcatccagc cagaaagtga gggagccacg
4601 gttgatgaga gctttgttgt aggtggacca gttggtgatt tgaactttt
4651 gctttgccac ggaacggtct gcgttgtcgg gaagatgcgt gatctgatcc
4701 ttcaactcag caaaagttcg atttattcaa caaagccgcc gtcccgtcaa
4751 gtcagcgtaa tgctctgcca gtgttacaac caattaacca attctgatta
4801 gaaaaactca tcgagcatca aatgaaactg caatttattc atatcaggat
4851 tatcaatacc atattttga aaaagccgtt tctgtaatga aggagaaaac
4901 tcaccgaggc agttccatag gatggcaaga tcctggtatc ggtctgcgat
4951 tccgactcgt ccaacatcaa tacaacctat taatttcccc tcgtcaaaaa
5001 taaggttatc aagtgagaaa tcaccatgag tgacgactga atccggtgag
5051 aatggcaaaa gcttatgcat ttctttccag acttgttcaa caggccagcc
5101 attacgctcg tcatcaaaat cactcgcatc aaccaaaccg ttattcattc
5151 gtgattgcgc ctgagcgaga cgaaatacgc gatcgctgtt aaaaggacaa
5201 ttacaaacag gaatcgaatg caaccggcgc aggaacactg ccagcgcatc
5251 aacaatattt tcacctgaat caggatattc ttctaatacc tggaatgctg
```

Figure 4 (cont'd)

```
5301 ttttcccggg gatcgcagtg gtgagtaacc atgcatcatc aggagtacgg
5351 ataaaatgct tgatggtcgg aagaggcata aattccgtca gccagtttag
5401 tctgaccatc tcatctgtaa catcattggc aacgctacct ttgccatgtt
5451 tcagaaacaa ctctggcgca tcgggcttcc catacaatcg atagattgtc
5501 gcacctgatt gcccgacatt atcgcgagcc catttatacc catataaatc
5551 agcatccatg ttggaattta atcgcggcct cgagcaagac gtttcccgtt
5601 gaatatggct cataacaccc cttgtattac tgtttatgta agcagacagt
5651 tttattgttc atgatgatat attttatct tgtgcaatgt aacatcagag
5701 attttgagac acaacgtggc tttccccccc ccccattat tgaagcattt
5751 atcagggtta ttgtctcatg agcggataca tatttgaatg tatttagaaa
5801 aataaacaaa taggggttcc gcgcacattt cccgaaaag tgccacctga
5851 cgtctaagaa accattatta tcatgacatt aacctataaa aataggcgta
5901 tcacgaggcc ctttcgtctc gcgcgtttcg gtgatgacgg tgaaaacctc
5951 tgacacatgc agctcccgga gacggtcaca gcttgtctgt aagcggatgc
6001 cgggagcaga caagcccgtc agggcgcgtc agcgggtgtt ggcgggtgtc
6051 ggggctggct taactatgcg gcatcagagc agattgtact gagagtgcac
6101 catatgcggt gtgaaatacc gcacagatgc gtaaggagaa aataccgcat
6151 cagattggct at
```

Figure 5

```
  1 MEKNGNNRKL RVCVATCNRA DYSKLAPIMF GIKTEPEFFE LDVVVLGSHL IDDYGNTYRM
 61 IEQDDFDINT RLHTIVRGED EAAMVESVGL ALVKLPDVLN RLKPDIMIVH GDRFDALALA
121 TSAALMNIRI LHIEGGEVSG TIDDSIRHAI TKLAHYHVCC TRSAEQHLIS MCEDHDRILL
181 AGCPSYDKLL SAKNKDYMSI IRMWLGDDVK SKDYIVALQH PVTTDIKHSI KMFELTLDAL
241 ISFNKRTLVL FPNIDAGSKE MVRVMRKKGI EHHPNFRAVK HVPFDQFIQL VAHAGCMIGN
301 SSCGVREVGA FGTPVINLGT RQIGRETGEN VLHVRDADTQ DKILQALHLQ FGKQYPCSKI
361 YGDGNAVPRI LKFLKSIDLQ EPLQKKFCFP PVKENISQDI DHILETLSAL AVDLGGTNLR
421 VAIVSMKGEI VKKYTQFNPK TYEERINLIL QMCVEAAAEA VKLNCRILGV GISTGGRVNP
481 REGIVLHSTK LIQEWNSVDL RTPLSDTLHL PVWVDNDGNC AALAERKFGQ GKGLENFVTL
541 ITGTGIGGGI IHQHELIHGS SFCAAELGHL VVSLDGPDCS CGSHGCIEAY ASGMALQREA
601 KKLHDEDLLL VEGMSVPKDE AVGALHLIQA AKLGNAKAQS ILRTAGTALG LGVVNILHTM
661 NPSLVILSGV LASHYIHIVK DVIRQQALSS VQDVDVVVSD LVDPALLGAA SMVLDYTTRR
721 IY*
```

Figure 6

```
NP_0011216996   1
NP_005467       1   METYGYLQRESCFQGPHELYFKNLSKRNKQIMEKNGNNRKLRVCVATCNRADYSKLAPIMFGIKTEPEFFELDVVVLGSH  80
NP_001177317    1   MEKNGNNRKLRVCVATCNRADYSKLAPIMFGIKTEPEFFELDVVVLGSH                                 49
NP_001177312    1   ---------------------------------MPIGDCSVAAKP-----------RKQLLC-------------------
NP_001177313    1   SLFQTTLGYRARASGWKPMVICRGSH                                                        44
                    MEKNGNNRKLRVCVATCNRADYSKLAPIMFGIKTEPEFFELDVVVLGSH                                 49
                    ------------------------------------------------

NP_0011216999  81   LIDDYGNTYRMIEQDDFDINTRLHTIVRGEDEAAMVESVGLALVKLPDVLNRLKPDIMIVHGDRFDALALATSAALMNIR  160
NP_005467      50   LIDDYGNTYRMIEQDDFDINTRLHTIVRGEDEAAMVESVGLALVKLPDVLNRLKPDIMIVHGDRFDALALATSAALMNIR  129
NP_001177317   45   AFKDLINTYRMIEQDDFDINTRLHTIVRGEDEAAMVESVGLALVKLPDVLNRLKPDIMIVHGDRFDALALATSAALMNIR  124
NP_001177312   50   LIDDYGNTYRMIEQDDFDINTRLHTIVRGEDEAAMVESVGLALVKLPDVLNRLKPDIMIVHGDRFDALALATSAALMNIR  129
NP_001177313    1   MIEQDDFDINTRLHTIVRGEDEAAMVESVGLALVKLPDVLNRLKPDIMIVHGDRFDALALATSAALMNIR             70

NP_0011216999 161   ILHIEGGEVSGTIDDSIRHAITKLAHYHVCCTRSAEQHLISMCEDHDRILLAGCPSYDKLLSAKNKDYMSIIRMWLGDDV  240
NP_005467     130   ILHIEGGEVSGTIDDSIRHAITKLAHYHVCCTRSAEQHLISMCEDHDRILLAGCPSYDKLLSAKNKDYMSIIRMWLGDDV  209
```

Figure 6 (cont'd)

```
NP_001177317  125  ILHIEGGEVSGTIDDSIRHAITKLAHYHVCCTRSAEQHLISMCEDHDRILLAGCPSYDKLLSAKNKDYMSIIRMWLGDDV  204
NP_001177312  130  ILHIEGGEVSGTIDDSIRHAITKLAHYHVCCTRSAEQHLISMCEDHDRILLAGCPSYDKLLSAKNKDYMSIIRMWLGDDV  209
NP_001177313   71  ILHIEGGEVSGTIDDSIRHAITKLAHYHVCCTRSAEQHLISMCEDHDRILLAGCPSYDKLLSAKNKDYMSIIRMWLG---  147

NP_001121699  241  KSKDYIVALQHPVTTDIKHSIKMFELTLDALISFNKRTLVLFPNIDAGSKEMVRVMRKKGIEHHPNFRAVKHVPFDQFIQ  320
NP_005467     210  KSKDYIVALQHPVTTDIKHSIKMFELTLDALISFNKRTLVLFPNIDAGSKEMVRVMRKKGIEHHPNFRAVKHVPFDQFIQ  289
NP_001177317  205  KSKDYIVALQHPVTTDIKHSIKMFELTLDALISFNKRTLVLFPNIDAGSKEMVRVMRKKGIEHHPNFRAVKHVPFDQFIQ  284
NP_001177312  210  KSKDYIVALQHPVTTDIKHSIKMFELTLDALISFNKRTLVLFPNIDAGSKEMVRVMRKKGIEHHPNFRAVKHVPFDQFIQ  289
NP_001177313  148  ----------------------------------------------SKEMVRVMRKKGIEHHPNFRAVKHVPFDQFIQ  179

[ ** GNE Allosteric domain ** ]
                                                     TLVLFPNIDAGSKEMVRVMRKKGIEHHPNFR
GNE pR263Q                                             Q
GNE pR263W                                             W
GNE pR263L                                             L
GNE pR266Q                                                Q
GNE pR266W                                                W NP_001121699  321  LVAHAGCMIGNSSCGVREVGAFGTPVINLGTRQIGRETGENVLHVRDADTQDKILQALHLQFGKQYPCSKIYGDGNAVPR  400
NP_005467b    290  LVAHAGCMIGNSSCGVREVGAFGTPVINLGTRQIGRETGENVLHVRDADTQDKILQALHLQFGKQYPCSKIYGDGNAVPR  369
```

Figure 6 (cont'd)

```
NP_001177317  285  LVAHAGCMIGNSSCGVREVGAFGTPVINLGTRQIGRETGENVLHVRDADTQDKILQALHLQFGKQYPCSKIYGDNAVPR  364
NP_001177312  290  LVAHAGCMIGNSSCGVREVGAFGTPVINLGTRQIGRETGENVLHVRDADTQDKILQALHLQFGKQYPCSKIYGDGNAVPR  369
NP_001177313  180  LVAHAGCMIGNSSCGVREVGAFGTPVINLGTRQIGRETGENVLHVRDADTQDKILQALHLQFGKQYPCSKIYGDNAVPR  259

NP_001121699  401  ILKFLKSIDLQEPLQKKFCFPPVKENISQDIDHILETLSALAVDLGGTNLRVAIVSMKGEIVKKYTQFNPKTYEERINLI  480
NP_005467b    370  ILKFLKSIDLQEPLQKKFCFPPVKENISQDIDHILETLSALAVDLGGTNLRVAIVSMKGEIVKKYTQFNPKTYEERINLI  449
NP_001177317  365  ILKFLKSIDLQEPLQKKFCFPPVKENISQDIDHILETLSALAVDLGGTNLRVAIVSMKGEIVKKYTQFNPKTYEERINLI  444
NP_001177312  370  ILKFLKSIDLQEPLQKKFCFPPVKENISQDIDHILETLSALAVDLGGTNLRVAIVSMKGEIVKKYTQFNPKTYEERINLI  449
NP_001177313  260  ILKFLKSIDLQEPLQKKFCFPPVKENISQDIDHILETLSALAVDLGGTNLRVAIVSMKGEIVKKYTQFNPKTYEERINLI  339

NP_001121699  481  LQMCVEAAAEAVKLNCRILGVGISTGGRVNPREGIVLHSTKLIQEWNSVDLRTPLSDTLHLPVWVDNDGNCAALAERKFG  560
NP_005467b    450  LQMCVEAAAEAVKLNCRILGVGISTGGRVNPREGIVLHSTKLIQEWNSVDLRTPLSDTLHLPVWVDNDGNCAALAERKFG  529
NP_001177317  445  LQMCVEAAAEAVKLNCRILGVGISTGGRVNPREGIVLHSTKLIQEWNSVDLRTPLSDTLHLPVWVDNDGNCAALAERKFG  524
NP_001177312  450  LQMCVEAAAEAVKLNCRILGV---------------------------------------------------------  470
NP_001177313  340  LQMCVEAAAEAVKLNCRILGVGISTGGRVNPREGIVLHSTKLIQEWNSVDLRTPLSDTLHLPVWVDNDGNCAALAERKFG  419
```

Figure 6 (cont'd)

```
NP_001121699  561 QGKGLENFVTLITGTGIGGGIIHQHELIHGSSFCAAELGHIVVSLDGPDCSCGSHGCIEAYASGMALQREAKKLHDEDLL 640
NP_005467b    530 QGKGLENFVTLITGTGIGGGIIHQHELIHGSSFCAAELGHIVVSLDGPDCSCGSHGCIEAYASGMALQREAKKLHDEDLL 609
NP_001177317  525 QGKGLENFVTLITGTGIGGGIIHQHELIHGSSFCAAELGHIVVSLDGPDCSCGSHGCIEAYASGMALQREAKKLHDEDLL 604
NP_001177312  471 ----------------------------------------------------------------------
NP_001177313  420 GIGGGIIHQHELIHGSSFCAAELGHIVVSLDGPDCSCGSHGCIEAYASGMALQREAKKLHDEDLL 535
              QGKGLENFVTLITGTGIGGGIIHQHELIHGSSFCAAELGHIVVSLDGPDCSCGSHGCIEAYASGMALQREAKKLHDEDLL 499

NP_001121699  641 LVEGMSVPKDEAVGALHLIQAAKLGNAKAQSILRTAGTALGLGVVNILHTMNPSLVILSGVLASHYIHIVKDVIRQQALS 720
NP_005467b    610 LVEGMSVPKDEAVGALHLIQAAKLGNAKAQSILRTAGTALGLGVVNILHTMNPSLVILSGVLASHYIHIVKDVIRQQALS 689
NP_001177317  605 LVEGMSVPKDEAVGALHLIQAAKLGNAKAQSILRTAGTALGLGVVNILHTMNPSLVILSGVLASHYIHIVKDVIRQQALS 684
NP_001177312  536 LVEGMSVPKDEAVGALHLIQAAKLGNAKAQSILRTAGTALGLGVVNILHTMNPSLVILSGVLASHYIHIVKDVIRQQALS 615
NP_001177313  500 LVEGMSVPKDEAVGALHLIQAAKLGNAKAQSILRTAGTALGLGVVNILHTMNPSLVILSGVLASHYIHIVKDVIRQQALS 579

NP_001121699  721 SVQDVDVVVSDLVDPALLGAASMVLDYTTRRIY 753
NP_005467b    690 SVQDVDVVVSDLVDPALLGAASMVLDYTTRRIY 722
NP_001177317  685 SVQDVDVVVSDLVDPALLGAASMVLDYTTRRIY 717
NP_001177312  616 SVQDVDVVVSDLVDPALLGAASMVLDYTTRRIY 648
NP_001177313  580 SVQDVDVVVSDLVDPALLGAASMVLDYTTRRIY 612
```

METHODS AND COMPOSITIONS FOR INCREASING SIALIC ACID PRODUCTION AND TREATING SIALIC RELATED DISEASE CONDITIONS

RELATED APPLICATIONS

The present application is a continuation of Ser. No. 13/364,181, filed Feb. 1, 2012, now abandoned, which in turn claims priority to the U.S. Provisional Application Ser. No. 61/438,585, filed Feb. 1, 2011, by Darvish et al., the entire disclosure of both of which is incorporated by reference herein, including the drawings.

FIELD OF THE INVENTION

The present invention is in the field of gene therapy methods and compositions for increasing production of sialic acid in a biological system by delivering the DNA coding region of the key enzyme of Sialic Acid biosynthesis (UDP-N-Acetylglucosamine 2-Epimerase/N-Acetylmannosamine Kinase, GNE)

BACKGROUND OF THE DISCLOSURE

Hereditary Inclusion Body Myopathy (HIBM) is a young-adult onset progressive skeletal muscle wasting disorder, which causes severe physical incapacitation. There is currently no effective therapeutic treatment for HIBM. HIBM is an autosomal recessive disorder caused by mutation in the GNE gene. The GNE gene encodes for the bifunctional enzyme UDP-GlcNAc 2-epimerase/ManNAc kinase (GNE/MNK). This is the key rate-limiting enzyme catalyzing the first two reactions of cellular sialic acid production. Reduced sialic acid production consequently leads to decreased sialyation of a variety of glycoproteins, including critical muscle proteins such as α-dystroglycan (α-DG), neural cell adhesion molecule (NCAM), or neprilysin, or lead to altered expression of other genes such as ganlioside (GM3) synthase. This in turn leads to muscle degeneration. HIBM is also known as Distal Myopathy with Rimmed Vacuoles, Nonaka Myopathy, Vacuolar myopathy sparing the quadricepts, or GNE related myopathy.

SUMMARY OF THE INVENTION

Disclosed herein are methods of expressing UDP-GlcNAc 2-Epimerase/ManNAc Kinase enzyme (GNE) peptide in a cell of a subject comprising: delivering into the cell of the subject an isolated nucleic acid expression construct that comprises a promoter operatively linked to a nucleic acid sequence encoding a GNE peptide or a therapeutically active fragment thereof, wherein the GNE peptide has the amino acid sequence of SEQ ID NO:3, wherein upon the delivering into the cell of the subject, the nucleic acid expression construct initiates expression of the GNE peptide or a therapeutically active fragment thereof.

Also disclosed are methods of delivering an encoded GNE enzyme comprising: a) creating an intravenous access at a point below a knee or an elbow of a limb of a subject; b) applying a tourniquet at a point proximal to the rest of the body of the subject than the intravenous access point; c) introducing a single dose of an isolated nucleic acid expression construct into the limb through the intravenous access, wherein the single dose is of sufficient volume to increase intravascular pressure for extravasation of the polynucleotide; wherein, the isolated nucleic acid construct comprises a promoter operatively linked to a nucleic acid sequence encoding a GNE peptide or a therapeutically active fragment thereof, wherein the GNE peptide has the amino acid sequence of SEQ ID NO:3.

Further, disclosed are methods of producing a GNE peptide in a cell comprising infecting the cell with an isolated nucleic acid construct that comprises a promoter operatively linked to a nucleic acid sequence encoding a GNE peptide or a therapeutically active fragment thereof, wherein the GNE peptide has the amino acid sequence of SEQ ID NO:3.

BRIEF DESCRIPTION OF THE DRAWINGS

FIG. 2 shows the nucleotide sequence of NTC8685-GNE vector (SEQ ID NO:1).

FIG. 4 shows the nucleotide sequence of UMVC3-GNE vector (SEQ ID NO:2).

FIG. 5 shows the amino acid sequence of GNE protein enzyme (SEQ ID NO:3).

FIG. 6 shows the amino acid sequence of GNE isoforms and Allosteric domain. Common allosteric domain mutations allowing higher Sialic Acid production are illustrated (R263Q/W/L, and R266Q/W).

DETAILED DESCRIPTION OF THE EMBODIMENTS

Disclosed herein are gene therapy methods and compositions for increasing production of sialic acid in a biological system by delivering the DNA coding region of the key enzyme of Sialic Acid biosynthesis (UDP-N-Acetylglucosamine 2-Epimerase/N-Acetylmannosamine Kinase, GNE). Disease conditions that will benefit from increased cellular sialic production, or enhanced GNE functions, include, but not limited to, Hereditary Inclusion Body Myopathy (HIBM) or Distal Myopathy with Rimmed Vacuoles (DMRV). The present methods and compositions also relate to reducing or eliminating non-human sialic acids (e.g. N-Glycolylneuraminate, Neu5Gc) from human cells or tissues. Non-human sialic acids may contribute to various human diseases, and long term reduction of cellular levels of non-human sialic acid may prove beneficial in preventing and treating those disease processes (WO/2010/030666) (Varki 2009). Increasing cellular production of Acetylneuraminate (Neu5Ac) can reduce cellular content of non-human sialic acids.

Being personally affected by HIBM, the inventor has developed and validated a gene therapy vector (plasmid, naked polynucleic acid) through in-vitro studies over the past 7 years. Through many years of medical literature searches, and evaluation of the data regarding various in-vivo delivery methods and vectors, an elegant and facile delivery method was chosen using a variation of a procedure known as the "Bier Block". Bier Block has been used safely in medical practice for over 100 years (dos Reis 2008).

As described below, the combination of the specific disease processes, the plasmids, and delivery method has numerous advantages over any others described to date. These advantages allow for facile translation for practical use in human and animal models.

Disclosed herein are the components of pharmacologic products and methods of delivering the pharmacologic products to the skeletal muscles or other organs (e.g. liver) of animals or human patient (e.g. patient affected with HIBM). The pharmacologic products can be polynucleotides encoding the unmodified or modified forms of GNE protein, polypeptides or amino acid sequences and/or or recombinant proteins, polypeptides or amino acid sequences encoded by the unmodified or modified forms of GNE nucleotide. In some embodiments, the delivery methods include (1) external or internal occlusion of major vessels (arteries, veins, and/or lymphatic system) to achieve vascular isolation of the target organ systems, group of organs/tissues, or body area, and (2) administration of the therapeutic product using vascular (e.g. intravenous) access. In some embodiments, the body organs/tissues/area that are isolated (target organs) are exposed to the compound being delivered, while in other embodiments, the body organs/tissues/area are protected from such exposure.

Description and Improvements of the Therapeutic Gene (GNE)

Figure 3:
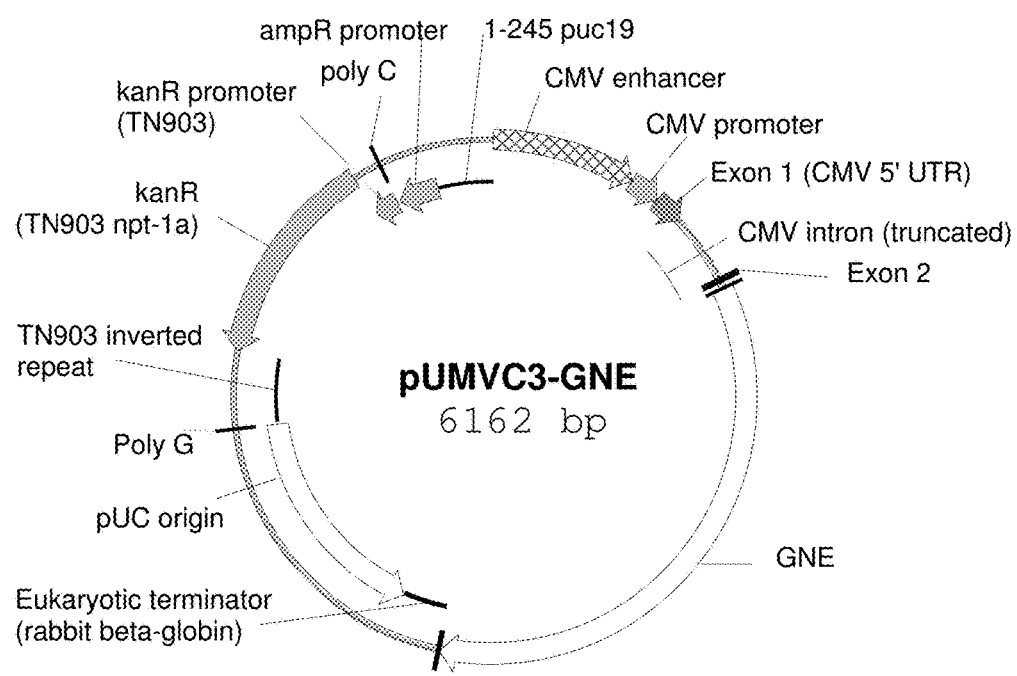
FIG. 3 is a diagram of UMVC3-GNE vector.

In some embodiments, the therapeutic products disclosed herein are polynucleotide (DNA) molecules, while in other embodiments, they are polypeptide (protein, protein fragments, amino acid sequences) molecules. In some embodiments, the polynucleotide molecule, either linear or circular, may contain various elements in addition to the coding sequence that encodes for the GNE protein, or a modified form of the GNE protein, that is or becomes biologically active within a biological system. GNE protein has the sequence (FIG. 3).

In some embodiments, the therapeutic methods disclosed herein are commonly known as "Gene Therapy", and comprise the administration of the above polynucleotide molecule. In other embodiments, the therapeutic methods disclosed herein are commonly known as "Enzyme Replacement Therapy (ERT)", and comprise the administration of the GNE protein, or a modified form of the GNE protein, that is or becomes biologically active within a biological system.

GNE encodes for the key enzyme of sialic acid production (UDP-N-Acetylglucosamine 2-epimerase/N-Acetylmannosamine Kinase). Several disease conditions can benefit from increased expression of GNE. The most notable being the severely debilitating progressive muscle wasting disorder known as GNE related myopathy, Hereditary Inclusion Body Myopathy (HIBM) and one of its distinct forms known as IBM2, or Distal Myopathy with Rimmed Vacuoles (DMRV)

The GNE enzyme components or domains (e.g. series of 10 or more sequential amino acids) may be recombined to enhance desired functions of the GNE gene and reduce or eliminate undesired functions. For example, if production of high amounts of sialic acid (NeuAc) is desired in biological organisms, for example prokaryotes or eukaryotes, one may optimize the epimerase domain of the GNE gene to eliminate or reduce the allosteric inhibitory domain function. In organisms and animals having redundant ManNAc kinase activity, such as other enzymes able to efficiently perform phosphorylation of ManNAc, one may also reduce or eliminate the GNE kinase domain to reduce the size, the minimum effective dose, and/or maximize the maximum tolerable dose in a biological system.

Although the GNE enzyme, or various components or domains thereof, is also known to have cellular functions besides production of sialic acid (Hinderlich, Salama et al. 2004; Broccolini, Gliubizzi et al. 2005; Krause, Hinderlich et al. 2005; Salama, Hinderlich et al. 2005; Penner, Mantey et al. 2006; Wang, Sun et al. 2006; Amsili, Shlomai et al. 2007; Amsili, Zer et al. 2008; Kontou, Weidemann et al. 2008; Kontou, Weidemann et al. 2009; Paccalet, Coulombe et al. 2010), hyposialylation of critical cellular molecules play an important role in human disease process (Huizing, Rakocevic et al. 2004; Noguchi, Keira et al. 2004; Saito, Tomimitsu et al. 2004; Tajima, Uyama et al. 2005; Ricci, Broccolini et al. 2006; Galeano, Klootwijk et al. 2007; Sparks, Rakocevic et al. 2007; Nemunaitis, Maples et al. 2010).

Increasing sialic acid and NeuAc/NeuGc ratio in biological systems is desired for several known reasons in human subjects. Mammals produce two different sialic molecules: (1) N-Acetylneuraminic acid (NANA or Neu5Ac), and (2) N-Glycolylneuraminic acid (Neu5Gc). CMP-NANA is converted to CMP-Neu5Gc by CMP-NANA hydoxylase (CMAH). Unlike other primates and mammals (including cow), humans are genetically deficient in Neu5Gc due to an Alu-mediated inactivating mutation of CMAH (Chou, Hayakawa et al. 2002). Thus, Neu5Ac is the only sialic acid produced by humans and many humans produce antibodies against Neu5Gc (Tangvoranuntakul, Gagneux et al. 2003). The NeuGc found in human tissues and cells are believed to be from food or cell culture media. Humans produce antibodies against NeuGc, potentially contributing to chronic inflammation, and various common disorders in which chronic inflammation is believed to be a significant factor (e.g. cancer, atherosclerosis, autoimmune disorders) (Hedlund, Padler-Karavani et al. 2008; Varki 2009). NeuGc can also promote human diseases, such as hemolytic uremic syndrome (HUS). A major cause of HUS is Shiga toxigenic *Escherichia coli* (STEC) infection. A highly toxic Shiga toxin subtilase cytotoxin (SubAB) prefers binding to glycan terminating in NeuGc (Lofling, Paton et al. 2009). This information increases our concern that NeuGc may also increase human susceptibility to some infectious agents.

Thus, it is desired to increase the content of NeuAc (human sialic acid) in food, and reduce the proportion of NeuGc found in meat and milk products. A potentially effective method to accomplish this is to increase GNE expression, and reduce or eliminate the CMAH expression in biological systems or organism used as either human or animal food (e.g. milk, meat, diary, and other animal based products). CMAH may be reduced by either of genetic or metabolic technologies, including, but not limited to, genetic modification of animals to produce CMAH knock-out or knock-down animals, reduction of CMAH enzyme expression by polynucleotide technologies (expressed as inhibitory RNA or antisense oligonucleotide), or inhibition of CMAH enzyme by metabolic substrate analogues. NeuGc may also be reduced in biological systems by overexpression of the enzyme that converts NeuGc to NeuAc.

With few exceptions, plants do not typically produce sialic acid. GNE and other sialic acid pathway enzymes can be used in plant, vegetable, and fruit crops to increase sialic acid in food.

Modifications, additions, and/or removal of polynucleotide elements (e.g. promoters, enhancers, repeat elements)

can be used to enhance expression in various tissues/organs or developmental stages, which may be desired in various fields of biotechnology including, but not limited to, pharmacologic, food, and cosmetic industries.

Because skeletal muscle is an important tissue that is readily accessible and that is highly vascularized, it could be used as a factory to produce proteins with therapeutic values (reviewed in (Lu, Bou-Gharios et al. 2003; Ratanamart and Shaw 2006)). Indeed, it has been demonstrated that functional therapeutic proteins can be synthesized by the skeletal muscle and secreted into the blood circulation in sufficient amount to mitigate the pathology associated with disorders such as hemophilia, Pompe disease, Fabry's disease, anaemia, emphysema, and familial hypercholesterolemia. The ability to express recombinant proteins in skeletal muscle is also an important issue for the treatment of neuromuscular disorders such as Duchenne and limb girdle muscular dystrophy. These disorders are caused by mutations of a gene that produces an essential muscle protein One potential treatment for such disorders is gene transfer, whose objective is to introduce into the muscle a normal and functional copy of the gene that is mutated.

Thus, in one aspect, disclosed herein are methods to utilize muscle as protein factory to over-produce and secrete sialic acid. In some embodiments, the methods disclosed herein result in an increase of Neu5Ac biosynthesis in plasma, and the reduction of Neu5Gc concentration from cells.

Description and Improvement of the Therapeutic Product

In some embodiments, the therapeutic product is a polynucleotide, while in other embodiments, the therapeutic product is a polypeptide. In some embodiments, the polynucleotide is a DNA molecule, which can comprise the full-length coding region for a protein, the coding region for a domain of a protein, or a coding region for a protein fragment, which is shorter than a recognized and identified domain of a protein. Thus, the polynucleotides disclosed herein can range from oligomers of at least 15 base pairs in length to DNA molecule comprising the full-length coding region for a protein.

In some embodiments, the polypeptide is a full-length protein, e.g., an enzyme or a receptor, while in other embodiments, the polypeptide is a protein fragment. In some embodiments, the protein fragment corresponds to a recognized and identified domain of a full-length protein, while in other embodiments, the polypeptide is shorter than a recognized and identified domain of a protein. Thus, the polypeptides disclosed herein can range from oligomers of at least 5 amino acids in length to full-length proteins. In some embodiments, the protein fragment is a therapeutically active protein fragment. By "therapeutically active protein fragment" it is meant that the protein fragment under physiological conditions has the same biochemical activity (e.g., catalyzes the same reaction) as the wild-type GNE protein, although it may perform the function at a different rate.

In some embodiments, the polynucleotide is a linear DNA molecule whereas in other embodiments, the polynucleotide is a circular DNA molecule.

In some embodiments, the polynucleotide is a circular DNA (plasmid, miniplasmid, or minicircle) able to express the GNE gene in the desired biological system. The NTC8685 vector described in this application has few benefits, which include reduced size, reduced bacterial sequence content, and antibiotic free selection. Other vectors known to those of skill in the art can also be used with the methods described herein.

In some embodiments, the polynucleotide therapeutic product, whether linear or circular, is administered as naked DNA, combined with other molecules to produce various cationic or anaionic particles, or co-administered with other pharmacological agents (e.g. excipients, vasodialaters, analgesics, etc,) to maximize efficacy of therapy and minimize patient discomfort. Instead of a polynucleotide, other pharmacologic products may be administered using the stated delivery method.

Unlike in vitro studies, where net positive zeta potential is a more efficient cellular entry of a polyneuleotide, in vivo transduction of skeletal muscle seems to be more efficient using a polynucleotide having a net negative charge (PCT WO/2004/062368).

In one embodiment, muscle specific promoters may be used to reduce chance of host immune response against the transgene and enhance the duration of intramuscular expression of the transgene. The backbone plasmid elements can be altered to allow for muscle specific expression. The ability to achieve high-level and long-term recombinant protein expression after gene transfer in skeletal muscle is desired in many disease conditions. This can be achieved using promoters and enhancers specific for muscle.

Several different muscle specific promoters have been described to date. The muscle creatine kinase (MCK) promoter and truncated versions are the most common muscle specific promoters used (Hauser, Robinson et al. 2000; Yuasa, Sakamoto et al. 2002; Sun, Zhang et al. 2005; Sebestyen, Hegge et al. 2007; Wang, Li et al. 2008). The synthetic C5-12 promoter and similar promoters show promise of being muscle specific while driving high expression of transgene (Li, Eastman et al. 1999). This C5-12 promoter drives expression levels similar to the ubiquitous CMV promoters in AAV vectors (Gonin, Arandel et al. 2005). The C5-12 can be further improved by adding the MCK enhancer (E-Syn promoter) (Wang, Li et al. 2008). The hybrid α-myosin heavy chain enhancer-/MCK enhancer-promoter (MHCK7) promoter also was used for high expression in muscles (Salva, Himeda et al. 2007). The desmin promoter is also recently described as a muscle-specific promoter capable or driving high level expression in muscle cells (Pacak, Sakai et al. 2008; Talbot, Waddington et al. 2010). The upstream enhancer elements (USE, USEx3/ΔUSEx3) of genes such as the troponin gene is also a promising candidate for developing muscle specific promoters (WO 2008124934 20081023; Blain, Zeng et al. 2010).

As disclosed herein, the GNE-encoding sequences, and/or the associated delivery vehicles used therewith, may be targeted towards specific cell types, for example, muscle cells, muscle tissue, and the like. For example, the promoter associated with the GNE coding sequence can be made to express GNE only in specific tissues or developmental stages. Alternatively, the expression cassette can be packaged with other molecules, compounds, or biologic moieties (e.g. protein/carbohydrate/lipid containing molecules, part or whole antibody molecules, part or whole cytokine molecules, viral capsids) to generate a biological mixture or specific biological particles designed to bind to and enter specific cell types. This binding or affinity can facilitate the uptake of the DNA into the cell. For delivery into muscle, in particular, anionic, non-liposomal, DNA containing particles are well-suited. However, cationic (liposomal) as well as other DNA containing biological mixtures or particles are also suited for uptake into myopathic muscle with compromised cell wall. In some embodiments, these protein, carbohydrate, and/or lipd containing molecules targeting moieties are, but are not limited to, microbial, plant, microbial, or synthetic compounds (e.g. antibodies, cytokines, lectins, other large or small molecules).

Figure 1:
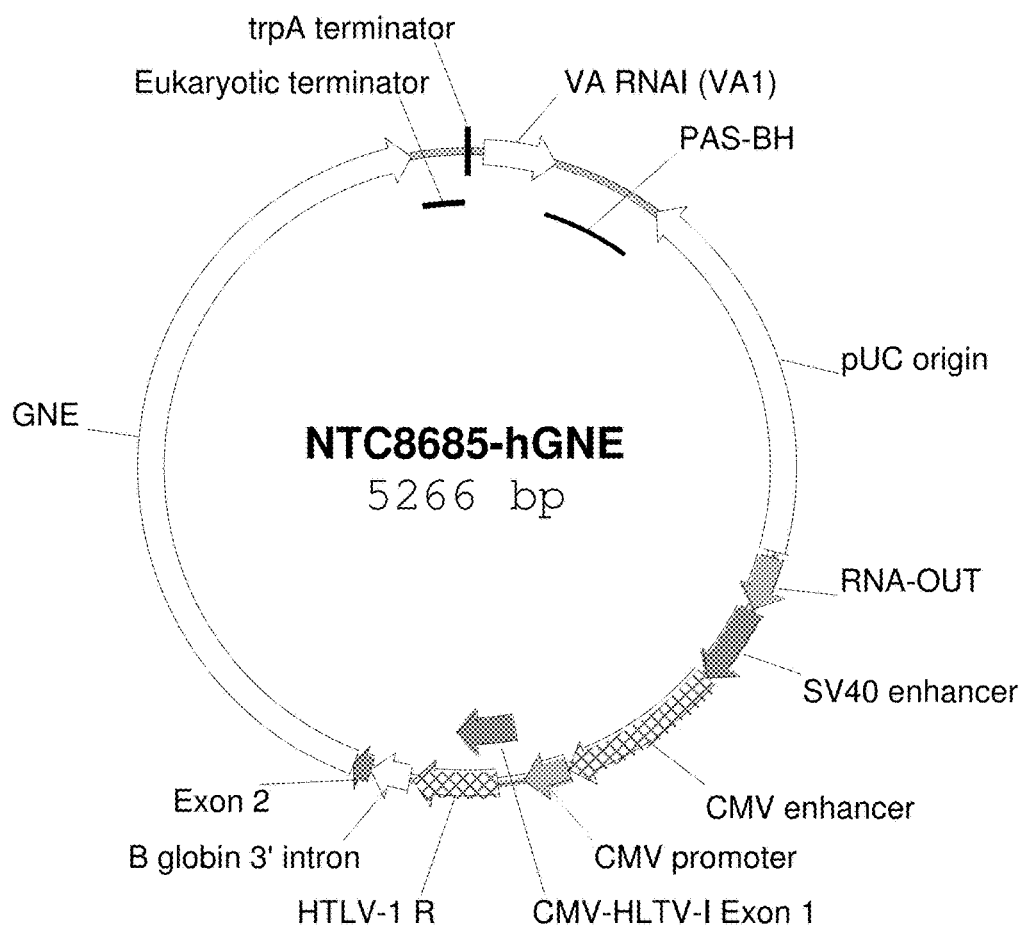
FIG. 1 is a diagram of the NTC8685-GNE expression vector described herein.

In some embodiments, polynucleotides products described herein comprise the following elements: 1) Bacterial Control Elements, which are active in bacteria for the purpose of selection and growth process, 2) Eukaryotic Control Elements, which are active in eukaryotic or mammalian cells for the purpose of expression of a therapeutic gene product or recombinant protein, and 3) the GNE coding region, which is the therapeutic gene product or recombinant gene. In some embodiments, prokaryotic/bacterial selection marker is based on antibiotic resistance (e.g. kanamycin resistance, as present in the UMVC3 vector, FIG. 3), or RNA based (e.g. RNA-OUT, present on the NTC8685 vector, FIG. 1). In other embodiments, other elements are used for efficient plasmid production (e.g. pUC orgin depicted in both UMVC3, FIG. 3, and NTC8684, FIG. 1) The nucleotide sequence of NTC8685-GNE vector is set forth in FIG. 2 and in SEQ ID NO:1, while the nucleotide sequence of UMVC3-GNE vector is set forth in FIG. 4. In additional embodiments, eukaryotic promoter, enhancer, introns or other elements are used for efficient transcription and translation of the therapeutic protein encoded by the GNE gene To minimize potential spread of antibiotic resistance, prokaryotic selection marker that is not based on antibiotic resistance is preferred by regulatory agencies such as World Heath Organization (WHO), US Food and Drug Administration (FDA), or European Agency for the Evaluation of Medicinal Products (EMEA) (Williams, Carnes et al. 2009).

Rationale for using plasmid DNA: Clinical use of naked or plasmid DNA (pDNA) to express therapeutic genes is a promising approach to treat muscle disease caused by IBM2. Naked DNA as gene therapy vehicle has an excellent safety record and repeat administration in the same subject can achieve higher expression levels. (Hagstrom, Hegge et al. 2004; Wolff, Lewis et al. 2005; Wolff, Budker et al. 2005; Herweijer and Wolff 2007; Braun 2008; Duan 2008; Zhang, Wooddell et al. 2009) Depending on method of delivery, pDNA delivered to skeletal muscle of rodents or primates is retained in myofibers and expresses the encoded gene product for many months (Danko, Fritz et al. 1993; Danko, Williams et al. 1997; Sebestyen, Hegge et al. 2007). Unlike Adeno-Associated Virus (AAV) and other viral vectors which can induce cellular or humoral immunity (Yuasa, Yoshimura et al. 2007; Mingozzi, Meulenberg et al. 2009), pDNA does not typically elicit an immune response against the vector (Hagstrom, Hegge et al. 2004; Romero, Braun et al. 2004; Glover, Lipps et al. 2005; Wolff, Budker et al. 2005), which makes it possible to repeat administrations in same subject. Additionally, compared to viral or based vectors, pDNA is relatively inexpensive to produce in large quantities and remains stable for many months (Walther, Stein et al. 2003; Urthaler, Ascher et al. 2007; Voss 2007).
Method of Delivery. Description and Improvement of the Delivery Method In one embodiment of the hydrodynamic infusion, an external tourniquet is placed on the limb of a human being or animal, and the therapeutic product is administered using a peripheral intravenous access using a specific volume (typically 30-50% of the limb volume below the tourniquet) in a specific amount of time or volume flow (typically 1-3 ml/second). This is very similar to commonly used medical procedures known as the "Bier Block", which has been used safely and effectively for more than a century to reduce the exposure and dose of pharmacologic compounds. Bier Block has been used to induce intravenous regional anesthesia (eliminating the need for general anesthesia) in arm or hand surgery (dos Reis 2008; Vlassakov and Bhavani 2010). Similar method is used in oncology by the name of "isolated limb infusion" for the administration of chemotherapeutic compounds to a specific limb, allowing for reduction in dose and exposure to internal organs (Kroon and Thompson 2009). Placing a tourniquet on limbs has also been used effectively for many centuries to reduce bleeding following severe trauma, or to reduce exposure of internal organs to toxins following exposure (e.g. venomous snake and other animal bites).

When administering gene therapy or biologics using the same or very similar delivery, the delivery method is described in medical literature by multiple names, including "hydrodynamic", "transvenular", "transvenous", "transvascular", "vascular", "retrograde", "limb vein", "peripheral vein", "intravenous", "intravascular", "retrograde", "extravasation", "high pressure", "pressurized", "isolated limb", "vascular isolation", "vascular occlusion", "blood flow occlusion", or any combination thereof (Su, Gopal et al. 2005; Sebestyen, Hegge et al. 2007; Vigen, Hegge et al. 2007; Zhang, Wooddell et al. 2009; Haurigot, Mingozzi et al. 2010; Hegge, Wooddell et al. 2010; Powers, Fan et al. 2010). Despite specific concerns, post-phlebitic syndrome or post-procedure angiopathy has not been noted following performance of vascular occlusion procedures following canine (dog) studies (Haurigot, Mingozzi et al. 2010).

In some embodiments, disclosed herein, the delivery method has been improved. Human and animal limbs of same volume may be composed of varying ratios of muscle and non-muscle (e.g. fatty or scar) tissues. Muscle is often more vascular and requires higher blood flow that lipid or scar tissue. Thus, administering therapeutic products using a specific volume may not confer optimum distribution of the therapeutic product in limbs of individuals. Limbs with higher muscle/non-muscle tissue may require higher infusion volumes to achieve same therapeutic benefit. Controlling the infusion based on intravascular (or infusion line) pressure and duration of infusion may convey improved distribution of therapeutic product to the target limb. The following alterations of the described method accordingly improve this delivery method:
1) Placing the tourniquet of specific pressure roughly 2-4× the systolic pressure (e.g. 320 mmHg for a human patient).
2) Rapid increase of flow to achieve a specific intravascular (or infusion line) pressure typically below the tourniquet pressure (e.g. if tourniquet pressure is maintained at 320 mmHg, the infusion line pressure maintained 280-300 mmHg)
3) Maintaining the infusion line pressure by controlling infusion flow rate.
4) Maintaining the infusion line pressure for a specific duration of time (15 minutes).
5) Using a specifically designed device to safely achieve parameters described above in 1 and 2. Such device may automatically control the flow rate and pressure of the infusion line based on the set tourniquet pressure. For safety, such device would automatically stop infusion (flow rate of zero mL/sec) upon detection of parameters such as sudden drop in infusion line pressure, air bubble within the infusion line, or fluid level within the container holding the fluid to be infused.

By selecting the site of vascular administration distal or proximal to the site of vascular occlusion, one can either expose or protect the target organs, tissues, or body area.

Rationale for using HLV delivery method: Although commonly used for DNA vaccination trials, pDNA delivered by instramuscular (IM) approach is inefficient for muscle diseases demanding delivery of therapeutic product to an entire limb or the whole body (Jiao, Williams et al. 1992). Intravenous (IV) plasmid is cleared rapidly by the liver (Liu, Shollenberger et al. 2007). However, combined with hydrodynamic limb vein (HLV) delivery, pDNA administered IV can effectively and uniformly transfect skeletal muscle of an entire limb in small and large animals including non-human primates (Hagstrom, Hegge et al. 2004), that results in reversible microvasculature damage (Toumi, Hegge et al. 2006; Vigen, Hegge et al. 2007). A single dose can result in long-term gene expression, and the ease of repeat administration makes HLV suitable for delivering GNE transgene to the limbs of IBM2 patients. Using a tourniquet, blood flow in an arm or leg temporarily occluded, and a plasmid DNA solution is rapidly injected intravenously. This elevates the pressure within the occluded region, leading to remarkably efficient migration of the gene vehicle into the adjoining myofibers. Blood flow is restored to normal in 10-20 minutes, with no irreversible or persistent adverse affects. Similar high pressure intravenous approaches are being adopted and adapted for delivery of DNA, and possibly other potential therapeutic molecules, to various organs. (Al-Dosari, Knapp et al. 2005; Arruda, Stedman et al. 2005; Wolff, Lewis et al. 2005; Herweijer and Wolff 2007; Toromanoff, Cherel et al. 2008).

IBM2/DMRV is an ideal orphan disorder to be treated by pDNA gene delivery using HLV for the following reasons:

Low GNE expression may be therapeutic: GNE gene is relatively small (cDNA size 2,169 bp, coding for 722 amino acids), functioning as a protein enzyme that is expressed at low levels in skeletal muscle. Expression of low amounts of wild-type, or very low amounts of sialuria form of GNE, may prove remarkably effective or even curative. Additionally, it is possible to use the hypermorphic (Sialuria) form of the GNE gene allowing for very low expressions of the GNE gene to translate to significant therapeutic benefit. This is in sharp contrast to other muscle diseases such as Duchenne' or Becker muscular dystrophies where relatively large amounts of dystrophin (or truncated mini-dystrohpin) are needed to realize therapeutic benefit.

Treating limbs alone may be sufficient therapy: IBM2 notably affects muscles of arms and legs. Trunk muscles are clinically affected later in disease course. Vital organs, including heart and lungs, are not clinically affected in vast majority of patients. By saving arm and leg function, we can significantly improve quality of life and delay loss of independence.

Host immune response to the transgene is unlikely: Over 99% of known patients express GNE protein that differs from wild-type by one amino acid (mis sense mutation). Additionally, GNE is evolutionarily conserved with 98% homology between mice and men at the amino acid level. Thus, the chance of host immune response or producing neutralizing antibodies against the GNE transgene is minimal. Coupling GNE with a muscle specific promoter such as creatine kinase (CK) further reduces chance of host antibody response (Fabre, Bigey et al. 2006).

Potential for beneficial bystander or distant effects: Unlike dystrophinopathies, where expression of dystrophin (large structural protein) within a myofiber seems to benefit only the site of injection, in IBM2 it is likely that Neu5Ac (small molecule, 9 carbon sugar) will not remain within a limited region of the myofiber. Neu5Ac produced by one myofiber may benefit neighboring myofibers, and ManNAc or Neu5Ac in serum may benefit the myofibers exposed to that serum. Following data further support this hypothesis: (a) Sia deficient mouse models are able to use Neu5Ac present in serum (Malicdan, Noguchi et al. 2009) (b) hyposialylated cells became re-sialylated after their growth medium was supplemented with ManNAc (Schwarzkopf, Knobeloch et al. 2002) and (c) adding 5 mM ManNAc or Neu5Ac, but not GlcNAc, to the media restored the sialic acid content of primary DMRV fibroblasts or myotubes from 60-75% of control to normal levels (Noguchi, Keira et al. 2004). Bystander effect, and possibility of distant effect, was observed in a recent single patient trial (Nemunaitis, Maples et al. 2010). The patient received GNE-lipoplex intramuscular injection of forearm (Extensor Carpi Radialis Longus, ECRL). Transient increase in strength, recombinant GNE (rGNE) expression, and increase of cell surface sialic acid was observed at the injection site and adjacent compartment muscles. Possibility of distant effect was also suggested following the surprising observation that distant muscle groups (trapezius and quadriceps) improved transiently in correlation with left ECRL rGNE transgene expression and increased sialylation (Nemunaitis, Maples et al. 2010).

Safety/Toxicology

Based on available information, GNE plasmid is expected to be a very safe vector for use in IBM2 patients. Generally, naked DNA as gene therapy vehicle has an excellent safety record and repeat administration in the same subject can achieve higher expression levels. (Hagstrom, Hegge et al. 2004; Wolff, Lewis et al. 2005; Wolff, Budker et al. 2005; Herweijer and Wolff 2007; Braun 2008; Duan 2008; Zhang, Wooddell et al. 2009).

Safety of GNE plasmid: Rodent toxicology studies using GNE-plasmid are currently underway. Preliminary data suggests naked plasmid will prove much safer than GNE-lipoplex that has already been administered to a human patient (Phadke, Jay et al. 2009; Nemunaitis, Maples et al. 2010). We conducted a recent pre-GLP toxicology study of 14 day duration on 12 mice (strain B6; FBV mixed inbred, 6 male and 6 female of age 4-10 months). Male and female mice were divided equally and randomly into experiment and control groups. The experiment group received high dose GNE plasmid (0.6 mg suspended in 0.1 ml normal saline) administered via IV tail, and the control group received only 0.1 ml normal saline. The groups were further divided into 3 dose frequency groups of 2 mice (1 female, 1 male) each as follows: 1) every day administration for 14 days, 2) every other day administration, and 3) once per week. All animals survived the experiment. No significant change were observed between the experiment and the control groups with respect to all measured parameters, which included body weights, temperature, food and water intake, CBC blood tests (performed at pre-dose day 1 and at necropsy on day 15). No significant change in the gross pathology was observed between the experiment and the control groups with respect to 12 organs, including brain, lung, heart, liver, kidney, spleen, stomach, intestines, bladder, genitals, lymph nodes, and muscle. The daily human equivalent dose (HED) was 120 mg, and the maximum 14 day total HED was 1440 mg.

Safety of GNE-lipoplex: In comparison to naked plasmid GNE, the GNE-lipoplex form is more toxic. To produce the lipoplex, the plasmid vector was encapsulated in a cationic liposome composed of 1,2-dioleoyl-3-trimethylammonium-propane (DOTAP) and cholesterol (GNE-lipoplex). The vector was injected into BALB/c mice, and ingle intravenous (IV) infusion of GNE-lipoplex was lethal in 33% of animals at 100 µg (0.1 mg) dose, with a small proportion of animals in the 40 µg cohort demonstrating transient toxicity (Phadke, Jay et al. 2009). Based on a poster presented at 2010 ASGCT conference (Phadke, Jay et al. 2010), the maximum tolerated dose for administration of multiple injections of GNE-lipoplex in Balb/c mice was (1) 20 µg per injection (Human equivalent dose (HED)=5.2 mg), or (2) a cumulative dose of 80 µg (HED=20.8 mg). In the ongoing dose escalation trial, the patient has received several infusions (0.4, 0.4, 1.0 mg) of 1-3 months apart, and transient grade 1, 2 tachycardia and fever were observed within 12 hours of each infusion. Patient's liver function tests were also reported as transiently elevated, but exact numbers were not reported in the abstract (Nemunaitis, Jay et al. 2010).

Safety of Hydrodynamic Limb Vein (HLV) delivery method: Potential side effect of the hydrodynamic delivery method has been studied in non-human primates at double the tourniquet pressures proposed for the current study. The procedure was determined to be safe, without any non-reversible or long-lasting side effects (Vigen, Hegge et al. 2007; Hegge, Wooddell et al. 2010). Its procedure is similar to the Bier Block used for regional anesthesia and surgical homeostasis that has been used safely and effectively for over a century. The main difference is that exsanguination is unnecessary and duration of the procedure is typically 15 minutes in HLV (Hegge, Wooddell et al. 2010). Histologic studies in non-human primates have shown that the HLV procedure caused transient muscle edema but no significant muscle damage (Hagstrom, Hegge et al. 2004; Toumi, Hegge et al. 2006). T2-weighted MRI images in non-human primates also showed that the procedure caused transient muscle edema but there was no persistent muscle derangement such as a compartment syndrome (Vigen, Hegge et al. 2007). Magnetic resonance angiography in nonhuman primates revealed vascular effects consistent with a transient effect on capillary permeability but no long-term abnormalities of concern (Vigen et al., 2007). These initial studies were performed using much higher tourniquet pressures (700 mmHg) than we are proposing (310 mmHg). Also, the injection volume of 45-50% of the limb volume was used in these studies, and we are proposing an injection/limb volume of 35%. We believe the plasmid will enter myopathic fibers more effectively than normal muscle due to reduced integrity of the muscle cell walls, thus justifying the reduced pressures and injection volumes. Using these similar pressures, a volume escalation study in adult patients suffering from muscular dystrophy is underway at University of North Carolina, Chapel Hill (Powers, Fan et al. 2010).

In summary, the HLV delivery method using pDNA is considered mature technology that has proven effective and safe in non-human primates, and is ready to be tested in clinical therapeutic trials (Wells 2004; Al-Dosari, Knapp et al. 2005; Herweijer and Wolff 2007). The main disadvantage of this approach is the inability to easily transfect diaphragm, heart, and trunk/neck muscles without invasive methods to temporarily clamp the major internal vessels (e.g. surgical, laparoscopic, or transcutaneous balloon-occlusion). Although this disadvantage is significant for many muscular dystrophies, it is not nearly as important in patients affected by IBM2. Many IBM2 patients live into their senior years, their heart and lungs have not been reported to become clinically affected, trunk/neck muscles seem to remain strong until late in disease course, and there exists significant potential for bystander or distant effect. Thus, HLV delivery of pDNA for delivering GNE transgene to limb skeletal muscles is an attractive therapeutic option for IBM2 that may delay loss of physical independence, and offer significant hope for many IBM2 patients.

The GNE-encoding sequences and related compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated composition or its delivery form. For example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent. Among the acceptable vehicles and solvents that may be employed are water, Ringer's solution, U. S. P. and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid may be used in the preparation of injectables.

According to certain embodiments, a Plasma-Lyte® carrier may be employed and used to deliver a GNE-encoding sequence, particularly for parenteral injection. (Baxter Laboratories, Inc., Morton Grove, Ill.). Plasma-Lyte® is a sterile, non-pyrogenic isotonic solution that may be used for intravenous administration. Each 100 mL volume contains 526 mg of Sodium Chloride, USP (NaCl); 502 mg of Sodium Gluconate ($C_6H_{11}NaO_7$); 368 mg of Sodium Acetate Trihydrate, USP ($C_2H_3NaO_2 \cdot H_2O$); 37 mg of Potassium Chloride, USP (KCl); and 30 mg of Magnesium Chloride, USP ($MgCl_2 \cdot 6H_2O$). It contains no antimicrobial agents. The pH is preferably adjusted with sodium hydroxide to about 7.4 (6.5 to 8.0).

The injectable formulations used to deliver GNE-encoding sequences may be sterilized, for example, by filtration through a bacterial-retaining filter, or by incorporating sterilizing agents in the form of sterile solid compositions, which can be dissolved or dispersed in sterile water, Plasma-Lyte® or other sterile injectable medium prior to use.

In order to prolong the expression of a GNE-encoding sequence within a system (or to prolong the effect thereof), it may be desirable to slow the absorption of the composition from subcutaneous or intramuscular injection. This may be accomplished by the use of a liquid suspension of crystalline or amorphous material with poor water solubility. The rate of absorption of the composition may then depend upon its rate of dissolution, which, in turn, may depend upon crystal size and crystalline form.

Alternatively, delayed absorption of a parenterally administered GNE-encoding sequence may be accomplished by dissolving or suspending the composition in an oil vehicle. Injectable depot forms may be prepared by forming microencapsule matrices of the GNE-encoding sequence in biodegradable polymers such as polylactide-polyglycolide. Depending upon the ratio of GNE-encoding sequence material to polymer and the nature of the particular polymer employed, the rate of GNE-encoding sequence release can be controlled. Examples of other biodegradable polymers include poly(orthoesters) and poly(anhydrides). As described above, depot injectable formulations may also be prepared by entrapping the GNE-encoding sequence in liposomes (or even microemulsions) that are compatible with the target body tissues, such as muscular tissue.

In addition to methods for modulating the production of sialic acid in a system, the present invention further encompasses methods for producing wild-type GNE in a system. According to such embodiments, the system (e.g., the muscle cells of a human patient) may comprise a mutated endogenous GNE-encoding sequence (e.g., the GNE- M712T sequence). In other words, the present invention includes providing, for example, a cell or muscular tissue that harbors a mutated (defective) GNE-encoding sequence with a functional wild-type GNE encoding sequence. The wild-type GNE encoding sequence may be delivered to such a system using, for example, the liposomes or lipid nanoparticles described herein, via parenteral injection.

According to additional related embodiments of the present invention, methods for treating, preventing, and/or ameliorating the effects of Hereditary Inclusion Body Myopathy (HIBM2) are provided. Such methods generally comprise providing a patient with a therapeutically effective amount of a wild-type GNE-encoding nucleic acid sequence. In certain embodiments, the wild-type GNE-encoding nucleic acid sequence may, preferably, be delivered to a patient in connection with a lipid nanoparticle and a carrier similar to that of Plasma-Lyte®, via parenteral injection.

The phrase "therapeutically effective amount" of a wild-type GNE-encoding nucleic acid sequence refers to a sufficient amount of the sequence to express sufficient levels of wild-type GNE, at a reasonable benefit-to-risk ratio, to increase sialic acid production in the targeted cells and/or to otherwise treat, prevent, and/or ameliorate the effects of HIBM2 in a patient. It will be understood, however, that the total daily usage of the wild-type GNE-encoding nucleic acid sequence and related compositions of the present invention will be decided by the attending physician, within the scope of sound medical judgment.

One of the advantages of the methods described herein is that, because the polynucleotides are administered to the affected limb directly, as opposed to a systemic administration, the therapeutically effective amount that is administered is less than that in the methods described previously. Therefore, the present methods reduce or eliminate many of the side effects that are associated with the methods described previously.

The specific therapeutically effective dose level for any particular patient may depend upon a variety of factors, including the severity of a patient's HIBM2 disorder; the activity of the specific GNE-encoding sequence employed; the delivery vehicle employed; the age, body weight, general health, gender and diet of the patient; the time of administration, route of administration, and rate of excretion of the specific GNE-encoding sequence employed; the duration of the treatment; drugs used in combination or contemporaneously with the specific GNE-encoding sequence employed; and like factors well-known in the medical arts.

Upon improvement of a patient's condition, a maintenance dose of a GNE-encoding sequence may be administered, if necessary. Subsequently, the dosage or frequency of administration, or both, may be reduced, as a function of the symptoms, to a level at which the improved condition is retained when the symptoms have been alleviated to the desired level.

According to yet further embodiments of the invention, novel compositions are provided for expressing wild-type GNE in a system. The compositions preferably include a wild-type GNE-encoding nucleic acid sequence. As described herein, the GNE-encoding nucleic acid sequence may comprise various transcriptional control elements, such as a promoter, termination sequence, and others. A non-limiting example of a composition encompassed by the present invention includes the pUMVC3-GNE expression vector described herein, shown in FIG. 3. so as described relative to other embodiments of the present invention, the GNE-encoding nucleic acid sequence may be disposed within or connected to an appropriate vehicle for delivery to a system, such as a liposome or lipid nanoparticle. Still further, according to such embodiments, the delivery vehicle may, optionally, be decorated with agents that are capable of recognizing and binding to target cells or tissues, such as muscle cells or muscle tissues.

EXAMPLES

Example 1—Expression of Exogenous GNE in CHO-Lec3 Cells

In the following example, several GNE expression vectors from human cDNA were created. Three different GNE forms, wild type, M712T, and R266Q, were robustly expressed in GNE deficient cells (Lec3 cells). All enzymes demonstrated similar protein expression levels, albeit distinct enzymatic activities. As the following will show, the transfected GNE expressing cell lines produced significantly more sialic acid than untransfected cells.

Methodology.

First Procedure:

GNE Cloning. Parental vectors containing the GNE cDNA were provided by Daniel Darvish (HIBM Research Group, Encino, Calif.) and included pGNE-NB8 (wild type), pGNE-MB18 (M712T mutant), and pGNE-R266Q (R266Q mutant). The destination vector, pUMVC3, was purchased from Aldevron (Fargo, N. Dak.). The subcloning vector, pDrive (Qiagen, Valencia, Calif.)1 was used to shuttle the R266Q mutant from the parent vector to the destination vector.

GNE cDNA inserts (wildtype and M712T) were produced by reverse transcription of RNA isolated from patient whole blood. The R266Q isoform was produced using standard mutagenesis PCR techniques using specifically designed primers. cDNA was then amplified using specifically designed primers bearing EcoR1 and BamH1 recognition 5' tails, and subsequently subcloned into the pUMVC3 expression vector (Aldevron) by T4 ligation (Invitrogen). Competent *E. coli* cells (Invitrogen) were then transformed with the pUMVC3 expression vector.

Positive pUMVC3-GNE clones were grown overnight in 175 mis LB broth+50 µg/ml Kan and 150 mis culture was used for a Qiagen (Valencia, Calif.) HiSpeed Plasmid Maxi kit according to the manufacturer protocols.

DNA. lipid complex. The DNA:lipid complex used in this example was produced by mixing, at room temperature, 1,2-Dioleoyl-3-Trimethylammonium-Propane (DOTAP) with test DNA (pUMVC3-GNE). DOTAP is a commercially-available lipid particle that is offered by Avanti Polar Lipids, Inc. (Alabaster, Ala.). The DOTAP was mixed with the pUMVC3-GNE DNA in a manner to achieve the desired total volume, which exhibited a final ratio of 0.5 µg DNA: 4 mM DOTAP1 in a final volume of 1 µl.

Cell Culture. GNE-deficient CHO-Lec3 cells were provided by Albert Einstein College of Medicine. The cells were grown at 37° C. in 5% $CO_2$ in α-MEM media supplemented with 4 mM L-glutamine and 10% heat inactivated, Fetal Bovine Serum. Cells for transient transfections were plated at 1×106 cells per well in 6-well plates and grown overnight. Lec3 cells were weaned to reduced serum conditions by reducing the FBS by 2.5% per passage.

Transient Transfections. Lec3 cells were transfected for 6 hours with DNA:lipid complex per well in OptiMEM (Invitrogen, Carlsbad Calif.), then the media was changed to normal α-MEM growth media and the cells were cultured overnight. DNA:lipid complexes were formed by mixing 4 µg DNA+10 µl Lipofectamine 2000 (Invitrogen) according to the manufacturers protocol. Twenty-four hours post-transfection, cells were harvested by trypsin digest and washed once with PBS before subsequent western blot or enzyme/sugar assays.

Sialic Acid Quantitation. Approximately 4×106 cells were used for the quantification of membrane-bound sialic acid by the thiobarbituric acid method. Cells were resuspended in water and lysed by passage through a 25 gauge needle 20 times and centrifuged. The supernatant was used for Bradford protein estimation and the remaining pellet was resuspended in 100 µl 2M acetic acid and incubated for 1 hour at 800 C to release glycoconjugate-bound sialic acids. 137 µl of periodic acid solution (2.5 mg/ml in 57 mM $H_2SO_4$) were added and incubated for 15 minutes at 37° C. Next, 50 µl of sodium arsenite solution (25 mg/ml in 0.5 M HCl) were added and the tubes were shaken vigorously to ensure complete elimination of the yellow-brown color. Following this step, 100 µl of 2-thiobarbituric acid solution (71 mg/ml adjusted to pH 9.0 with NaOH) were added and the samples were heated to 100° C. for 7.5 minutes. The solution was extracted with 1 ml of butanol/5% 12M HCl and the phases were separated by centrifugation. The absorbance of the organic phase was measured at 549 nm. The amount of sialic acid was measured as nmol sialic acid/mg of protein.

Second Procedure:

The following procedure is an alternative procedure to the one described above.

Cell culturing and biological assay testing: Lec3 CHO cells (Hong 2003) obtained from Dr. Pamela Stanley (Albert Einstein College of Medicine) were initially grown in α-MEM media containing 10% fetal bovine serum (FBS) (Invitrogen), received subsequent passages of α-MEM FBS medium by 2.5% decrements until 0% FBS, and trypsinized prior to transfection. Four sets of transfections were prepared in triplicate using 2.0×106 CHO cells, 2.5 mL of Freestyle Media (Invitrogen), 500 µl of Opti-MEM (Invitrogen), 10 µl of Lipofectamine (Invitrogen) and 4 µg of DNA (except for the no vector set) and incubated at 37° C. in 5% $CO_2$. Sets prepared included GNE wild-type pUMVC3 vector, GNE M712T pUMVC3 vector, GNE R266Q pUMVC3 vector, empty vector, and no vector media. Cells were collected 48 hours post-transfection, washed with PBS, and resuspended in lysis buffer. Sialic acid content was detected using a modified version of the Leonard Warren method (Warren 1959) and measured with NanoDrop-1000 Spectrophotometer (Thermo Fisher Scientific) at 549 nm using the UBV-Vis module. A standard curve was created with known sialic acid concentrations and denoted a clear linear association between absorbance and sialic acid concentration.

Results.

GNE clones. The GNE cDNA clones that were tested included a human wild type cDNA and two human mutant cDNAs. The mutants included the M712T GNE deficient clone and the R266Q sialuria clone. Sialuria is a human disease caused by point mutations in the CMP-sialic acid binding site of GNE, leading to a loss of feedback inhibition and mass production of sialic acids. GNE cDNAs were subcloned from their original vectors to the expression vector, pUMVC3, by restriction digest cloning. Clones were screened by directional restriction enzyme digest to confirm the GNE insert was in the correct orientation. Positive clones were sequenced in both orientations to confirm that no mutations occurred during the cloning process. The resulting chromatograms were compared against the GNE sequence from GenBank (accession #NM_005467) and the wild type did not exhibit any mutations, while the M712T and R266Q clones contained only the expected point mutations. Positive pUMVC3-GNE clones were scaled using a maxi prep plasmid purification procedure and sequenced again to confirm that no mutations occurred. These DNA stocks were used for all subsequent experiments.

Wt-GNE mRNA quantitation. CHO-Lec3 cells were grown in 10% serum and transiently transfected with pUMVC3-GNE-wt DNA for 24 hours to quantitate the amount of recombinant GNE RNA that was expressed. Total RNA was extracted and RT-qPCR was performed to amplify a 230 bp fragment from the GNE transcript. Serial dilutions of pUMVC3-GNE-wt were used to determine that the concentration of GNE-wt expressed in transfected Lec3 cells was equal to 4.1 pg/µl. The dynamic range of the qPCR was from 5 ng-5 fg and there was no GNE mRNA product detected in control (untransfected) CHO-Lec3 cells (the cT value for untransfected cells was greater than 42 cycles, which is less than 5 fg). Therefore, recombinant GNE mRNA expression was detected in transfected Lec3 cells, while untransfected cells had undetectable amounts of GNE mRNA.

Figure 7:
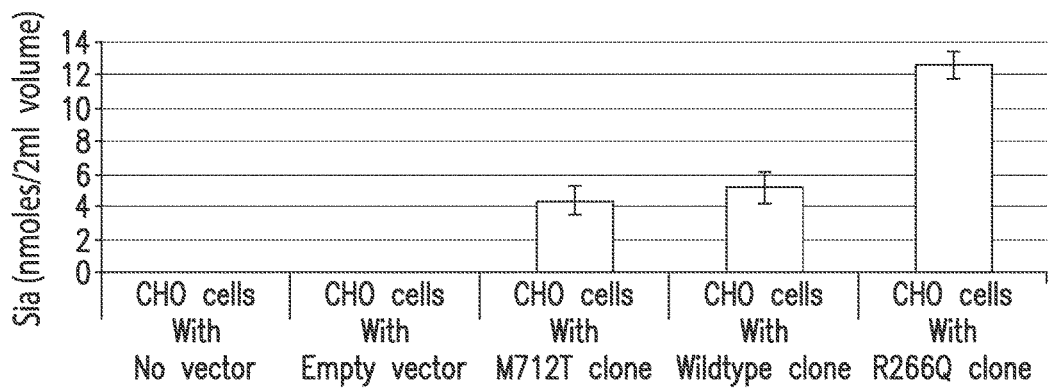
FIG. 7 is a bar graph of sialic acid production in GNE-null CHO cells. In comparison to untreated cells ("Media", "Empty Vector"), sialic acid production was significant greater in cells transfected with GNE plasmids.

Sialic acid assays. Transfected Lec3 cells also were tested for cell surface sialic acid expression. All Lec3 samples had approximately 6.0 nmol/mg membrane bound sialic acid, with the exception of Lec3 cells transfected with the R266Q GNE1 which had a 1.5-fold higher amount (FIG. 7). The R266Q GNE lacks the feedback inhibition of GNE and is known to cause an overproduction of intracellular sialic acids. Lec3 cells seem to be undersialylated, and this could only be overcome by expression of the sialuria mutant and not by the about 100-fold overexpression of wild-type GNE compared to wild-type CHO cells. No significant differences between wild type (wt) and M712T GNE were observed.

Figure 8:
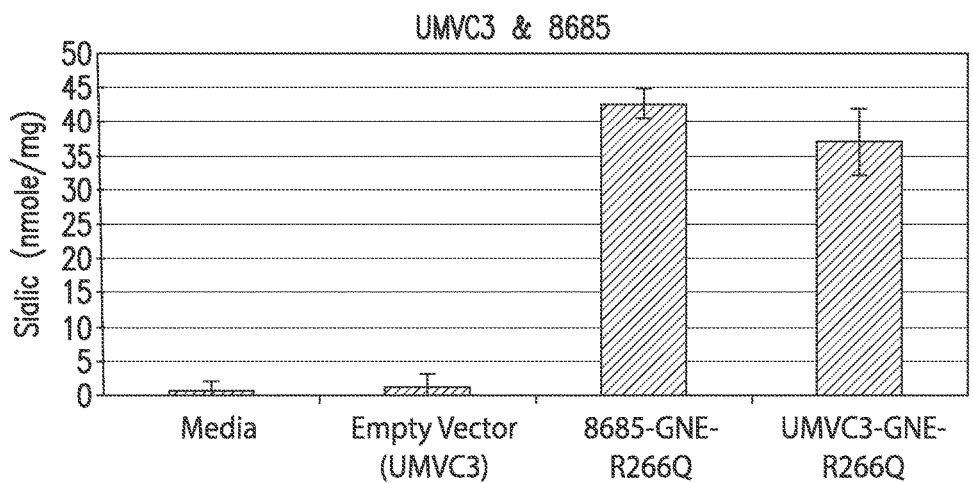
FIG. 8 is a bar graph of Sialic Acid GNE-null CHO cells, comparison of UMVC3 and NTC8685 Vectors.
Figure 9:
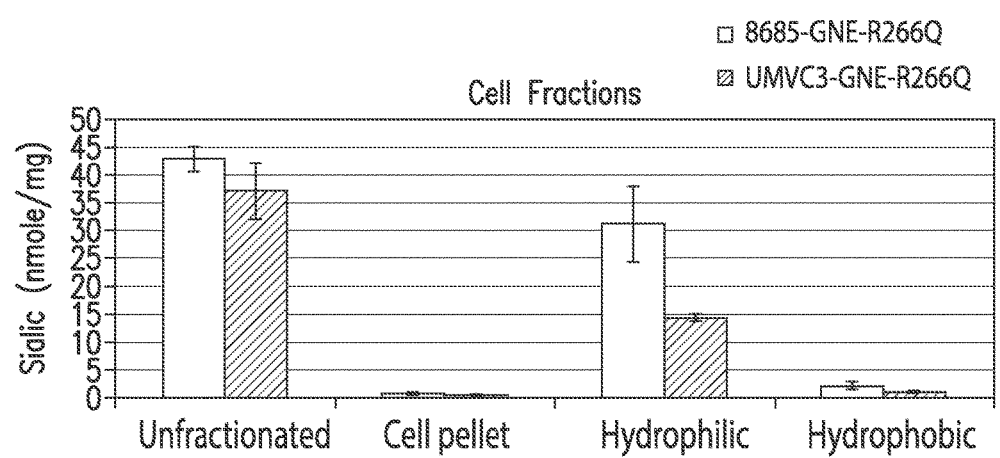
FIG. 9 is a bar graph of Sialic Acid content cell fractions of GNE-null CHO cells, comparison of UMVC3 and NTC8685 Vectors.

Comparison of UMVC3 and NTC8685 GNE plasmids: Transfection studies comparing sialic acid production of both vectors correlated well with each other (FIGS. 8 and 9). Slightly higher production of sialic acid was noted with NTC8685 vector. Additional in-vitro studies using other cell types and in-vivo studies will be conducted.

Figure 10:
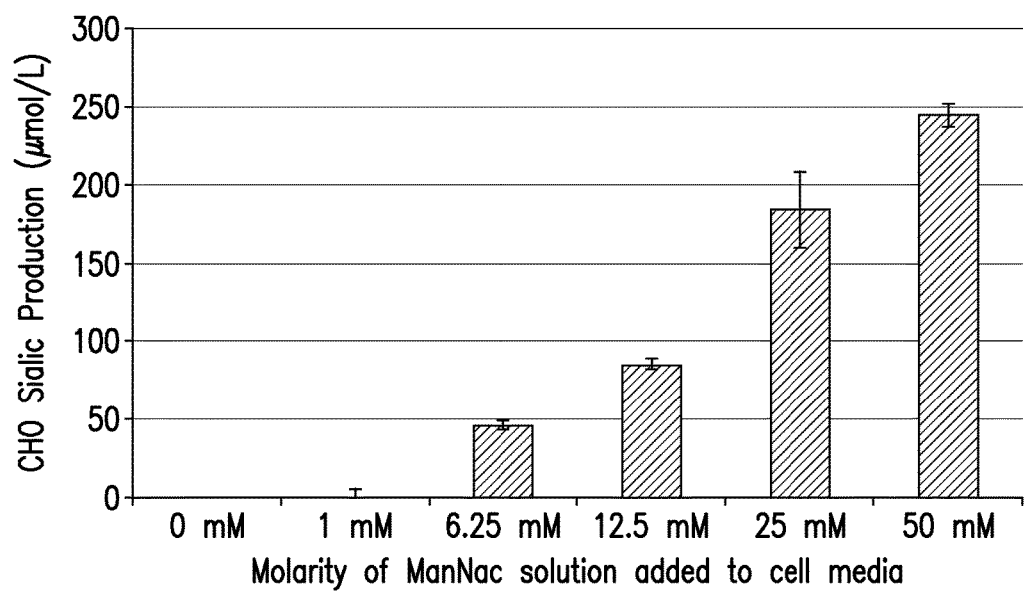
FIG. 10 is a bar graph showing the relative in-vitro dose comparison of GNE vecor vs ManNAc

Silic acid production by provision of ManNAc. The level of Sialic acid production was measured by supplementing cell culture media with N-Acetylmannosamine (ManNAc). Besides provision of ManNAc, all other cell culture variables were identical to transfection studies (FIG. 10).

Preliminary high dose plasmid toxicity. We conducted a recent pre-GLP toxicology study of 14 day duration on 12 mice (strain B6;FBV mixed inbred, 6 male and 6 female of age 4-10 months). Male and female mice were divided equally and randomly into experiment and control groups (Table 1). The maximum feasible dose (MFD) in a mouse model was 600 µg per injection. Limitation was based on solubility of plasmid (6 µg/µl) and total volume per injection (100 µL). Considering mouse weight of 30 g and human weight of 70 kg, the human equivalent dose (HED) for mouse dose of 600 µg is 113.82 mg.

TABLE 1

| Frequency of infusion | Mice | Weight (g) Day 1 | Toxicity 24 h | Toxicity 48 hr | Toxicity Day 7 | Weight Day 7 | Toxicity Day 14 | Weight Day 14 | Total Plasmid Dose |
|---|---|---|---|---|---|---|---|---|---|
| Control Group (100 normal saline) | | | | | | | | | |
| Every day | 1M | 29.54 | None | None | None | 28.8 | None | 28.96 | 0 |
|  | 1F | 29.99 | None | None | None | 26.6 | None | 26.74 | 0 |
| Every other day | 1M | 32.69 | None | None | None | 32.9 | None | 31.95 | 0 |
|  | 1F | 21.88 | None | None | None | 20.6 | None | 20.23 | 0 |
| Once per week (day 1 and 7) | 1M | 27.76 | None | None | None | 27.5 | None | 26.91 | 0 |
|  | 1F | 22.24 | None | None | None | 22.5 | None | 23.55 | 0 |
| Experiment Group (600 ug plasmid in 100 uL NS) | | | | | | | | | |
| Every day | 1M | 27.59 | None | None | None | 26.8 | None | 27.68 | 8.4 mg |
|  | 1F | 27.28 | None | None | None | 24.7 | None | 21.78 | 8.4 mg |
| Every other day | 1M | 31.54 | None | None | None | 29.6 | None | 29.39 | 4.2 mg |
|  | 1F | 23.35 | None | None | None | 21.9 | None | 23.71 | 4.2 mg |
| Once per week (day 1 and 7) | 1M | 30.37 | None | None | None | 28 | None | 29.8 | 1.2 mg |
|  | 1F | 24.55 | None | None | None | 23 | None | 23.38 | 1.2 mg |

The experiment group received high dose GNE plasmid (0.6 mg suspended in 0.1 ml normal saline) administered via IV by tail vein, and the control group received 0.1 ml normal saline. The groups were further divided into 3 dose frequency groups of 2 mice (1 female, 1 male) each as follows: 1) Every day administration for 14 days, 2) Every other day administration, and 3) Once per week. All animals survived the experiment. No significant change were observed between the experiment and the control groups with respect to all measured parameters, which included body weights, temperature, food and water intake, CBC blood tests (performed at days 1 and 15). Following necropsy on day 15, no significant change in the gross pathology was observed between the experiment and the control groups with respect to 12 organs, including brain, lung, heart, liver, kidney, spleen, stomach, intestines, bladder, genitals, lymph nodes, and muscle.

Although illustrative embodiments of the present invention have been described herein, it should be understood that the invention is not limited to those described, and that various other changes or modifications may be made by one skilled in the art without departing from the scope or spirit of the invention.

What is claimed is:

1. A pharmacologic product, comprising a DNA or RNA molecule having the sequence set forth in SEQ ID NO:1.

2. A cell containing the pharmacologic product of claim 1.

3. The product of claim 1 further comprising one or more pharmaceutically acceptable carriers, adjuvants or vehicles.

* * * * *

SEQUENCE LISTING

<160> NUMBER OF SEQ ID NOS: 14

<210> SEQ ID NO 1
<211> LENGTH: 5266
<212> TYPE: DNA
<213> ORGANISM: Homo sapiens

<400> SEQUENCE: 1

```
ccgcctaatg agcgggcttt tttttcttag ggtgcaaaag gagagcctgt aagcgggcac      60
tcttccgtgg tctggtggat aaattcgcaa gggtatcatg gcggacgacc ggggttcgag     120
ccccgtatcc ggccgtccgc cgtgatccat gcggttaccg cccgcgtgtc gaacccaggt     180
gtgcgacgtc agacaacggg ggagtgctcc ttttggcttc cttcccctac cggtctgcct     240
cgcgcgtttc ggtgatgacg gtgaaaacct ctgacacatg cagctcccgg agacggtcac     300
agcttgtctg taagcggatg ccgggagcag acaagcccgt cagggcgcgt cagcgggtgt     360
tggcgggtgt cggggcgcag ccatgaccca gtcacgtagc gatagcggag tgtatactgg     420
cttaactatg cggcatcaga gcagattgta ctgagagtgc accatatgcg gtgtgaaata     480
ccgcacagat gcgtaaggag aaaataccgc atcaggcgct cttccgcttc ctcgctcact     540
gactcgctgc gctcggtcgt tcggctgcgg cgagcggtat cagctcactc aaaggcggta     600
atacggttat ccacagaatc aggggataac gcaggaaaga acatgtgagc aaaaggccag     660
caaaaggcca ggaaccgtaa aaaggccgcg ttgctggcgt ttttccatag gctccgcccc     720
```

-continued

```
cctgacgagc atcacaaaaa tcgacgctca agtcagaggt ggcgaaaccc gacaggacta    780
taaagatacc aggcgtttcc ccctggaagc tccctcgtgc gctctcctgt tccgaccctg    840
ccgcttaccg gatacctgtc cgcctttctc ccttcgggaa gcgtggcgct ttctcatagc    900
tcacgctgta ggtatctcag ttcggtgtag gtcgttcgct ccaagctggg ctgtgtgcac    960
gaaccccccg ttcagcccga ccgctgcgcc ttatccggta actatcgtct tgagtccaac   1020
ccggtaagac acgacttatc gccactggca gcagccactg gtaacaggat tagcagagcg   1080
aggtatgtag gcggtgctac agagttcttg aagtggtggc ctaactacgg ctacactaga   1140
agaacagtat ttggtatctg cgctctgctg aagccagtta ccttcggaaa aagagttggt   1200
agctcttgat ccggcaaaca aaccaccgct ggtagcggtg gttttttgt ttgcaagcag    1260 cagattacgc gcagaaaaaa aggatctcaa gaagatcctt tgatcttttc tacggggtct   1320
gacgctcagt ggaacgaaaa ctcacgttaa gggattttgg tcatgagatt atcaaaaagg   1380
atcttcacct agatcctttt aaattaaaaa tgaagtttta atcaatcta aagtatatat    1440 gagtaaactt ggtctgacag ttaccaatgc ttaatcagtg aggcacctat ctcagcgatc   1500
tgtctatttc gttcatccat agttgcctga ctcctgcaaa ccacgttgtg gtagaattgg   1560
taaagagagt cgtgtaaaat atcgagttcg cacatcttgt tgtctgatta ttgattttg    1620 gcgaaaccat ttgatcatat gacaagatgt gtatctacct taacttaatg attttgataa   1680
aaatcattag gtacccctga tcactgtgga atgtgtgtca gttagggtgt ggaaagtccc   1740
caggctcccc agcaggcaga agtatgcaaa gcatgcatct caattagtca gcaaccaggt   1800
gtggaaagtc cccaggctcc ccagcaggca gaagtatgca aagcatgcat ctcaattagt   1860
cagcaaccat agtcccgccc ctaactccgc ccatcccgcc cctaactccg cccagttacg   1920
gggtcattag ttcatagccc atatatggag ttccgcgtta caacttacg ggtaaatggc    1980 ccgcctggct gaccgcccaa cgacccccgc ccattgacgt caataatgac gtatgttccc   2040
atagtaacgc caatagggac tttccattga cgtcaatggg tggagtattt acggtaaact   2100
gcccacttgg cagtacatca agtgtatcat atgccaagta cgccccctat tgacgtcaat   2160
gacggtaaat ggcccgcctg gcattatgcc cagtacatga ccttatggga ctttcctact   2220
tggcagtaca tctacgtatt agtcatcgct attaccatgg tgatgcggtt ttggcagtac   2280
atcaatgggc gtggatagcg gtttgactca cggggatttc caagtctcca ccccattgac   2340
gtcaatggga gtttgttttg gcaccaaaat caacgggact ttccaaaatg tcgtaacaac   2400
tccgccccat tgacgcaaat gggcggtagg cgtgtacggt gggaggtcta tataagcaga   2460
gctcgtttag tgaaccgtca gatcgcctgg agacgccatc cacgctgttt tgacctccat   2520
agaagacacc gggaccgatc cagcctccgc ggctcgcatc tctccttcac gcgcccgccg   2580
ccctacctga ggccgccatc cacgccggtt gagtcgcgtt ctgccgcctc ccgcctgtgg   2640
tgcctcctga actgcgtccg ccgtctaggt aagtttaaag ctcaggtcga ccgggcct     2700 ttgtccggcg ctcccttgga gcctacctag actcagccgg ctctccacgc tttgcctgac   2760
cctgcttgct caactctagt tctctcgtta acttaatgag acagatagaa actggtcttg   2820
tagaaacaga gtagtcgcct gcttttctgc caggtgctga cttctctccc ctgggctttt   2880 ttcttttct caggttgaaa agaagaagac gaagaagacg aagaagacaa accgtcgtcg    2940
acatggagaa gaatgaaat aaccgaaagc tgcgggtttg tgttgctact tgtaaccgtg    3000
cagattattc taaacttgcc ccgatcatgt ttggcattaa aaccgaacct gagttctttg   3060
aacttgatgt tgtggtactt ggctctcacc tgatagatga ctatggaaat acatatcgaa   3120
```

-continued

```
tgattgaaca agatgacttt gacattaaca ccaggctaca cacaattgtg aggggagaag    3180
atgaggcagc catggtggag tcagtaggcc tggcccagt  gaagctgcca gatgtcctta    3240
atcgcctgaa gcctgatatc atgattgttc atggagacag gtttgatgcc ctggctctgg    3300
ccacatctgc tgccttgatg aacatccgaa tccttcacat tgaaggtggg gaagtcagtg    3360
ggaccattga tgactctatc agacatgcca taacaaaact ggctcattat catgtgtgct    3420
gcacccgcag tgcagagcag cacctgatat ccatgtgtga ggaccatgat cgcatccttt    3480
tggcaggctg cccttcctat gacaaacttc tctcagccaa gaacaaagac tacatgagca    3540
tcattcgcat gtggctaggt gatgatgtaa aatctaaaga ttacattgtt gcactacagc    3600
accctgtgac cactgacatt aagcattcca taaaaatgtt tgaattaaca ttggatgcac    3660
ttatctcatt taacaagcgg accctagtcc tgtttccaaa tattgacgca gggagcaaag    3720
agatggttcg agtgatgcgg aagaagggca ttgagcatca tcccaacttt cgtgcagtta    3780
aacacgtccc atttgaccag tttatacagt tggttgccca tgctggctgt atgattggga    3840
acagcagctg tggggttcga gaagttggag cttttggaac acctgtgatc aacctgggaa    3900
cacgtcagat tggaagagaa acaggggaga atgttcttca tgtccgggat gctgacaccc    3960
aagacaaaat attgcaagca ctgcaccttc agtttggtaa acagtaccct tgttcaaaga    4020
tatatgggga tggaaatgct gttccaagga ttttgaagtt tctcaaatct atcgatcttc    4080
aagagccact gcaaaagaaa ttctgctttc ctcctgtgaa ggagaatatc tctcaagata    4140
ttgaccatat tcttgaaact ctaagtgcct tggccgttga tcttggcggg acgaacctcc    4200
gagttgcaat agtcagcatg aagggtgaaa tagttaagaa gtatactcag ttcaatccta    4260
aaacctatga agagaggatt aatttaatcc tacagatgtg tgtggaagct gcagcagaag    4320 ctgtaaaaact gaactgcaga attttgggag taggcatttc cacaggtggc cgtgtaaatc    4380
ctcgggaagg aattgtgctg cattcaacca aactgatcca agagtggaac tctgtggacc    4440
ttaggacccc cctttctgac actttgcatc tccctgtgtg ggtagacaat gatggcaact    4500
gtgctgccct ggcggaaagg aaatttggcc aaggaaaggg actggaaaac tttgttacac    4560
ttatcacagg cacaggaatc ggtggtggaa ttatccatca gcatgaattg atccacggaa    4620
gctccttctg tgctgcagaa ctgggccacc ttgttgtgtc tctggatggg cctgattgtt    4680
cctgtggaag ccatgggtgc attgaagcat acgcctctgg aatggccttg cagagggagg    4740
caaaaaagct ccatgatgag gacctgctct ggtggaagg gatgtcagtg ccaaaagatg    4800
aggctgtggg tgcgctccat ctcatccaag ctgcgaaact tggcaatgcg aaggcccaga    4860
gcatcctaag aacagctgga acagctttgg gtcttggggt tgtgaacatc ctccatacca    4920
tgaatccctc ccttgtgatc ctctccggag tcctggccag tcactatatc cacattgtca    4980
aagacgtcat tcgccagcag gccttgtcct ccgtgcagga cgtggatgtg gtggtttcgg    5040
atttggttga ccccgccctg ctgggtgctg ccagcatggt tctggactac acaacacgca    5100
ggatctacta gtaagatctt tttccctctg ccaaaaatta tggggacatc atgaagcccc    5160
ttgagcatct gacttctggc taataaagga aatttatttt cattgcaata gtgtgttgga    5220 atttttttgtg tctctcactc ggaaggacat aagggcggcc gctagc               5266
```

<210> SEQ ID NO 2
<211> LENGTH: 6162
<212> TYPE: DNA
<213> ORGANISM: Homo sapiens

```
<400> SEQUENCE: 2
tggccattgc atacgttgta tccatatcat aatatgtaca tttatattgg ctcatgtcca      60
acattaccgc catgttgaca ttgattattg actagttatt aatagtaatc aattacgggg     120
tcattagttc atagcccata tatggagttc gcgttacat aacttacggt aaatggcccg      180
cctggctgac cgcccaacga ccccgccca ttgacgtcaa taatgacgta tgttcccata     240
gtaacgccaa tagggactt ccattgacgt caatgggtgg agtatttacg gtaaactgcc      300
cacttggcag tacatcaagt gtatcatatg ccaagtacgc cccctattga cgtcaatgac     360
ggtaaatggc ccgcctggca ttatgcccag tacatgacct tatgggactt tcctacttgg     420
cagtacatct acgtattagt catcgctatt accatggtga tgcggttttg gcagtacatc     480
aatgggcgtg atagcggtt tgactcacgg ggatttccaa gtctccaccc cattgacgtc      540
aatgggagtt tgttttggca ccaaaatcaa cgggactttc caaaatgtcg taacaactcc     600
gccccattga cgcaaatggg cggtaggcgt gtacggtggg aggtctatat aagcagagct     660
cgtttagtga accgtcagat cgcctggaga cgccatccac gctgttttga cctccataga    720
agacaccggg accgatccag cctccgcggc cgggaacggt gcattggaac gcggattccc    780
cgtgccaaga gtgacgtaag taccgcctat agactctata ggcacacccc tttggctctt    840
atgcatgcta tactgttttt ggcttggggc ctatacaccc ccgcttcctt atgctatagg    900
tgatggtata gcttagccta taggtgtggg ttattgacca ttattgacca ctccaacggt    960
ggagggcagt gtagtctgag cagtactcgt tgctgccgcg cgcgccacca gacataatag   1020
ctgacagact aacagactgt tcctttccat gggtctttc tgcagtcacc gtcgtcgacg    1080
gtatcgataa gcttgatatc gaattcatgg agaagaatgg aaataaccga agctgcggg    1140 tttgtgttgc tacttgtaac cgtgcagatt attctaaact gccccgatc atgtttggca    1200 ttaaaaccga acctgagttc tttgaacttg atgttgtggt acttggctct cacctgatag   1260
atgactatgg aaatacatat cgaatgattg aacaagatga ctttgacatt aacaccaggc   1320
tacacacaat tgtgagggga aagatgagg cagccatggt ggagtcagta ggcctggccc    1380
tagtgaagct gccagatgtc cttaatcgcc tgaagcctga tatcatgatt gttcatggag   1440 acaggttga tgccctggct ctggccacat ctgctgcctt gatgaacatc cgaatccttc    1500
acattgaagg tggggaagtc agtgggacca ttgatgactc tatcagacat gccataacaa   1560
aactggctca ttatcatgtg tgctgcaccc gcagtgcaga gcagcacctg atatccatgt   1620
gtgaggacca tgatcgcatc ctttggcag gctgccttc ctatgacaaa cttctctcag    1680
ccaagaacaa agactacatg agcatcatc gcatgtggct aggtgatgat gtaaaatcta   1740
aagattacat tgttgcacta cagcaccctg tgaccactga cattaagcat tccataaaaa   1800
tgtttgaatt aacattggat gcacttatct catttaacaa gcggaccta gtcctgtttc    1860 caaatattga gcagggagc aaagagatgg ttcgagtgat gcggaagaag ggcattgagc    1920
atcatcccaa ctttcgtgca gttaaacacg tcccatttga ccagtttata cagttggttg   1980
cccatgctgg ctgtatgatt gggaacagca gctgtgggt tcgagaagtt ggagcttttg    2040
gaacacctgt gatcaacctg ggaacacgtc agattgaag agaaacaggg gagaatgttc    2100
ttcatgtccg ggatgctgac acccaagaca aaatattgca agcactgcac cttcagtttg   2160
gtaaacagta cccttgttca aagatatatg gggatgaaa tgctgttcca aggattttga    2220
agtttctcaa atctatcgat cttcaagagc cactgcaaaa gaaattctgc tttcctcctg   2280
tgaaggagaa tatctctcaa gatattgacc atattcttga aactctaagt gccttggccg   2340
```

```
ttgatcttgg cgggacgaac ctccgagttg caatagtcag catgaagggt gaaatagtta   2400
agaagtatac tcagttcaat cctaaaacct atgaagagag gattaattta atcctacaga   2460
tgtgtgtgga agctgcagca gaagctgtaa aactgaactg cagaattttg ggagtaggca   2520
tttccacagg tggccgtgta aatcctcggg aaggaattgt gctgcattca accaaactga   2580
tccaagagtg gaactctgtg gaccttagga ccccccttc tgacactttg catctccctg   2640
tgtgggtaga caatgatggc aactgtgctg ccctggcgga aggaaatttt ggccaaggaa   2700
agggactgga aaactttgtt acacttatca caggcacagg aatcggtggt ggaattatcc   2760
atcagcatga attgatccac ggaagctcct tctgtgctgc agaactgggc caccttgttg   2820
tgtctctgga tgggcctgat tgttcctgtg aagccatgg gtgcattgaa gcatacgcct    2880
ctggaatggc cttgcagagg gaggcaaaaa agctccatga tgaggacctg ctcttggtgg   2940
aagggatgtc agtgccaaaa gatgaggctg tgggtgcgct ccatctcatc caagctgcga   3000
aacttggcaa tgcgaaggcc cagagcatcc taagaacagc tggaacagct tgggtcttg   3060 gggttgtgaa catcctccat accatgaatc cctcccttgt gatcctctcc ggagtcctgg   3120
ccagtcacta tatccacatt gtcaaagacg tcattcgcca gcaggccttg tcctccgtgc   3180
aggacgtgga tgtggtggtt tcggatttgg ttgaccccgc cctgctgggt gctgccagca   3240
tggttctgga ctacacaaca cgcaggatct actaggatcc agatcttttt ccctctgcca   3300
aaaattatgg ggacatcatg aagcccttg agcatctgac ttctggctaa taaggaaat    3360 ttattttcat tgcaatagtg tgttggaatt ttttgtgtct ctcactcgga aggacatatg   3420
ggagggcaaa tcatttaaaa catcagaatg agtatttggt ttagagtttg gcaacatatg   3480
cccattcttc cgcttcctcg ctcactgact cgctgcgctc ggtcgttcgg ctgcggcgag   3540
cggtatcagc tcactcaaag gcggtaatac ggttatccac agaatcaggg gataacgcag   3600
gaaagaacat gtgagcaaaa ggccagcaaa aggccaggaa ccgtaaaaag gccgcgttgc   3660
tggcgttttt ccataggctc cgcccccctg acgagcatca caaaaatcga cgctcaagtc   3720
agaggtggcg aaacccgaca ggactataaa gataccaggc gtttccccct ggaagctccc   3780
tcgtgcgctc tcctgttccg accctgccgc ttaccggata cctgtccgcc tttctccctt   3840
cgggaagcgt ggcgctttct catagctcac gctgtaggta tctcagttcg gtgtaggtcg   3900
ttcgctccaa gctgggctgt gtgcacgaac cccccgttca gcccgaccgc tgcgccttat   3960
ccggtaacta tcgtcttgag tccaacccgg taagacacga cttatcgcca ctggcagcag   4020
ccactggtaa caggattagc agagcgaggt atgtaggcgg tgctacagag ttcttgaagt   4080
ggtggcctaa ctacggctac actagaagaa cagtatttgg tatctgcgct ctgctgaagc   4140
cagttacctt cggaaaaaga gttggtagct cttgatccgg caaacaaacc accgctggta   4200
gcggtggttt ttttgtttgc aagcagcaga ttacgcgcag aaaaaaagga tctcaagaag   4260
atcctttgat cttttctacg ggtctgacgc tcagtggaa cgaaaactca cgttaaggga   4320
ttttggtcat gagattatca aaaaggatct tcacctagat ccttttaaat taaaaatgaa   4380
gttttaaatc aatctaaagt atatatgagt aaacttggtc tgacagttac caatgcttaa   4440
tcagtgaggc acctatctca gcgatctgtc tatttcgttc atccatagtt gcctgactcg   4500 ggggggggg gcgctgaggt ctgcctcgtg aagaaggtgt tgctgactca taccaggcct   4560
gaatcgcccc atcatccagc cagaaagtga gggagcacg gttgatgaga gctttgttgt    4620
aggtggacca gttggtgatt ttgaactttt gctttgccac ggaacggtct gcgttgtcgg   4680
```

-continued

```
gaagatgcgt gatctgatcc ttcaactcag caaaagttcg atttattcaa caaagccgcc    4740
gtcccgtcaa gtcagcgtaa tgctctgcca gtgttacaac caattaacca attctgatta    4800
gaaaaactca tcgagcatca aatgaaactg caatttattc atatcaggat tatcaatacc    4860
atattttga aaaagccgtt tctgtaatga aggagaaaac tcaccgaggc agttccatag    4920
gatggcaaga tcctggtatc ggtctgcgat tccgactcgt ccaacatcaa taaacctat    4980
taatttcccc tcgtcaaaaa taaggttatc aagtgagaaa tcaccatgag tgacgactga    5040
atccggtgag aatggcaaaa gcttatgcat ttctttccag acttgttcaa caggccagcc    5100
attacgctcg tcatcaaaat cactcgcatc aaccaaaccg ttattcattc gtgattgcgc    5160
ctgagcgaga cgaaatacgc gatcgctgtt aaaaggacaa ttacaaacag gaatcgaatg    5220
caaccggcgc aggaacactg ccagcgcatc aacaatattt tcacctgaat caggatattc    5280
ttctaatacc tggaatgctg ttttcccggg gatcgcagtg gtgagtaacc atgcatcatc    5340
aggagtacgg ataaaatgct tgatggtcgg aagaggcata aattccgtca gccagtttag    5400
tctgaccatc tcatctgtaa catcattggc aacgctacct ttgccatgtt tcagaaacaa    5460
ctctggcgca tcgggcttcc catacaatcg atagattgtc gcacctgatt gcccgacatt    5520
atcgcgagcc catttatacc catataaatc agcatccatg ttggaattta atcgcggcct    5580
cgagcaagac gtttcccgtt gaatatggct cataacaccc cttgtattac tgtttatgta    5640
agcagacagt tttattgttc atgatgatat attttatct tgtgcaatgt aacatcagag    5700
attttgagac acaacgtggc tttccccccc ccccattat tgaagcattt atcagggtta    5760
ttgtctcatg agcggataca tatttgaatg tatttagaaa aataaacaaa tagggggttcc    5820
gcgcacattt ccccgaaaag tgccacctga cgtctaagaa accattatta tcatgacatt    5880
aacctataaa aataggcgta tcacgaggcc ctttcgtctc gcgcgtttcg gtgatgacgg    5940
tgaaaacctc tgacacatgc agctcccgga gacggtcaca gcttgtctgt aagcggatgc    6000
cgggagcaga caagcccgtc agggcgcgtc agcgggtgtt ggcgggtgtc ggggctggct    6060
taactatgcg gcatcagagc agattgtact gagagtgcac catatgcggt gtgaaatacc    6120
gcacagatgc gtaaggagaa ataccgcat cagattggct at                       6162
```

<210> SEQ ID NO 3
<211> LENGTH: 722
<212> TYPE: PRT
<213> ORGANISM: Homo sapiens

<400> SEQUENCE: 3

```
Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110
```

```
Arg Phe Asp Ala Leu Ala Leu Ala Thr Ser Ala Ala Leu Met Asn Ile
            115                 120                 125

Arg Ile Leu His Ile Glu Gly Gly Glu Val Ser Gly Thr Ile Asp Asp
130                 135                 140

Ser Ile Arg His Ala Ile Thr Lys Leu Ala His Tyr His Val Cys Cys
145                 150                 155                 160

Thr Arg Ser Ala Glu Gln His Leu Ile Ser Met Cys Glu Asp His Asp
                165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
        195                 200                 205

Val Lys Ser Lys Asp Tyr Ile Val Ala Leu Gln His Pro Val Thr Thr
    210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
                245                 250                 255

Gly Ser Lys Glu Met Val Arg Val Met Arg Lys Gly Ile Glu His
            260                 265                 270

His Pro Asn Phe Arg Ala Val Lys His Val Pro Phe Asp Gln Phe Ile
        275                 280                 285

Gln Leu Val Ala His Ala Gly Cys Met Ile Gly Asn Ser Ser Cys Gly
    290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
                325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
        355                 360                 365

Arg Ile Leu Lys Phe Leu Lys Ser Ile Asp Leu Gln Glu Pro Leu Gln
    370                 375                 380

Lys Lys Phe Cys Phe Pro Pro Val Lys Glu Asn Ile Ser Gln Asp Ile
385                 390                 395                 400

Asp His Ile Leu Glu Thr Leu Ser Ala Leu Ala Val Asp Leu Gly Gly
                405                 410                 415

Thr Asn Leu Arg Val Ala Ile Val Ser Met Lys Gly Glu Ile Val Lys
            420                 425                 430

Lys Tyr Thr Gln Phe Asn Pro Lys Thr Tyr Glu Glu Arg Ile Asn Leu
        435                 440                 445

Ile Leu Gln Met Cys Val Glu Ala Ala Ala Glu Ala Val Lys Leu Asn
    450                 455                 460

Cys Arg Ile Leu Gly Val Gly Ile Ser Thr Gly Gly Arg Val Asn Pro
465                 470                 475                 480

Arg Glu Gly Ile Val Leu His Ser Thr Lys Leu Ile Gln Glu Trp Asn
                485                 490                 495

Ser Val Asp Leu Arg Thr Pro Leu Ser Asp Thr Leu His Leu Pro Val
            500                 505                 510

Trp Val Asp Asn Asp Gly Asn Cys Ala Ala Leu Ala Glu Arg Lys Phe
        515                 520                 525

Gly Gln Gly Lys Gly Leu Glu Asn Phe Val Thr Leu Ile Thr Gly Thr
```

```
                    530                 535                 540
Gly Ile Gly Gly Gly Ile Ile His Gln His Glu Leu Ile His Gly Ser
545                 550                 555                 560

Ser Phe Cys Ala Ala Glu Leu Gly His Leu Val Val Ser Leu Asp Gly
                565                 570                 575

Pro Asp Cys Ser Cys Gly Ser His Gly Cys Ile Glu Ala Tyr Ala Ser
                580                 585                 590

Gly Met Ala Leu Gln Arg Glu Ala Lys Lys Leu His Asp Glu Asp Leu
                595                 600                 605

Leu Leu Val Glu Gly Met Ser Val Pro Lys Asp Glu Ala Val Gly Ala
610                 615                 620

Leu His Leu Ile Gln Ala Ala Lys Leu Gly Asn Ala Lys Ala Gln Ser
625                 630                 635                 640

Ile Leu Arg Thr Ala Gly Thr Ala Leu Gly Leu Gly Val Val Asn Ile
                645                 650                 655

Leu His Thr Met Asn Pro Ser Leu Val Ile Leu Ser Gly Val Leu Ala
                660                 665                 670

Ser His Tyr Ile His Ile Val Lys Asp Val Ile Arg Gln Gln Ala Leu
                675                 680                 685

Ser Ser Val Gln Asp Val Asp Val Val Ser Asp Leu Val Asp Pro
                690                 695                 700

Ala Leu Leu Gly Ala Ala Ser Met Val Leu Asp Tyr Thr Thr Arg Arg
705                 710                 715                 720

Ile Tyr

<210> SEQ ID NO 4
<211> LENGTH: 400
<212> TYPE: PRT
<213> ORGANISM: Homo sapiens

<400> SEQUENCE: 4

Met Glu Thr Tyr Gly Tyr Leu Gln Arg Glu Ser Cys Phe Gln Gly Pro
1               5                   10                  15

His Glu Leu Tyr Phe Lys Asn Leu Ser Lys Arg Asn Lys Gln Ile Met
                20                  25                  30

Glu Lys Asn Gly Asn Asn Arg Lys Leu Arg Val Cys Val Ala Thr Cys
                35                  40                  45

Asn Arg Ala Asp Tyr Ser Lys Leu Ala Pro Ile Met Phe Gly Ile Lys
        50                  55                  60

Thr Glu Pro Glu Phe Phe Glu Leu Asp Val Val Leu Gly Ser His
65                  70                  75                  80

Leu Ile Asp Asp Tyr Gly Asn Thr Tyr Arg Met Ile Glu Gln Asp Asp
                85                  90                  95

Phe Asp Ile Asn Thr Arg Leu His Thr Ile Val Arg Gly Glu Asp Glu
                100                 105                 110

Ala Ala Met Val Glu Ser Val Gly Leu Ala Leu Val Lys Leu Pro Asp
            115                 120                 125

Val Leu Asn Arg Leu Lys Pro Asp Ile Met Ile Val His Gly Asp Arg
130                 135                 140

Phe Asp Ala Leu Ala Leu Ala Thr Ser Ala Ala Leu Met Asn Ile Arg
145                 150                 155                 160

Ile Leu His Ile Glu Gly Gly Glu Val Ser Gly Thr Ile Asp Asp Ser
                165                 170                 175

Ile Arg His Ala Ile Thr Lys Leu Ala His Tyr His Val Cys Cys Thr
```

```
            180                 185                 190
Arg Ser Ala Glu Gln His Leu Ile Ser Met Cys Glu Asp His Asp Arg
        195                 200                 205
Ile Leu Leu Ala Gly Cys Pro Ser Tyr Asp Lys Leu Leu Ser Ala Lys
    210                 215                 220
Asn Lys Asp Tyr Met Ser Ile Ile Arg Met Trp Leu Gly Asp Asp Val
225                 230                 235                 240
Lys Ser Lys Asp Tyr Ile Val Ala Leu Gln His Pro Val Thr Thr Asp
                245                 250                 255
Ile Lys His Ser Ile Lys Met Phe Glu Leu Thr Leu Asp Ala Leu Ile
            260                 265                 270
Ser Phe Asn Lys Arg Thr Leu Val Leu Phe Pro Asn Ile Asp Ala Gly
        275                 280                 285
Ser Lys Glu Met Val Arg Val Met Arg Lys Lys Gly Ile Glu His His
    290                 295                 300
Pro Asn Phe Arg Ala Val Lys His Val Pro Phe Asp Gln Phe Ile Gln
305                 310                 315                 320
Leu Val Ala His Ala Gly Cys Met Ile Gly Asn Ser Ser Cys Gly Val
                325                 330                 335
Arg Glu Val Gly Ala Phe Gly Thr Pro Val Ile Asn Leu Gly Thr Arg
            340                 345                 350
Gln Ile Gly Arg Glu Thr Gly Glu Asn Val Leu His Val Arg Asp Ala
        355                 360                 365
Asp Thr Gln Asp Lys Ile Leu Gln Ala Leu His Leu Gln Phe Gly Lys
    370                 375                 380
Gln Tyr Pro Cys Ser Lys Ile Tyr Gly Asp Gly Asn Ala Val Pro Arg
385                 390                 395                 400

<210> SEQ ID NO 5
<211> LENGTH: 369
<212> TYPE: PRT
<213> ORGANISM: Homo sapiens

<400> SEQUENCE: 5

Met Glu Lys Asn Gly Asn Asn Arg Lys Leu Arg Val Cys Val Ala Thr
1               5                   10                  15
Cys Asn Arg Ala Asp Tyr Ser Lys Leu Ala Pro Ile Met Phe Gly Ile
            20                  25                  30
Lys Thr Glu Pro Glu Phe Phe Glu Leu Asp Val Val Leu Leu Gly Ser
        35                  40                  45
His Leu Ile Asp Asp Tyr Gly Asn Thr Tyr Arg Met Ile Glu Gln Asp
    50                  55                  60
Asp Phe Asp Ile Asn Thr Arg Leu His Thr Ile Val Arg Gly Glu Asp
65                  70                  75                  80
Glu Ala Ala Met Val Glu Ser Val Gly Leu Ala Leu Val Lys Leu Pro
                85                  90                  95
Asp Val Leu Asn Arg Leu Lys Pro Asp Ile Met Ile Val His Gly Asp
            100                 105                 110
Arg Phe Asp Ala Leu Ala Leu Ala Thr Ser Ala Ala Leu Met Asn Ile
        115                 120                 125
Arg Ile Leu His Ile Glu Gly Gly Glu Val Ser Gly Thr Ile Asp Asp
    130                 135                 140
Ser Ile Arg His Ala Ile Thr Lys Leu Ala His Tyr His Val Cys Cys
145                 150                 155                 160
```

Thr Arg Ser Ala Glu Gln His Leu Ile Ser Met Cys Glu Asp His Asp
            165                 170                 175

Arg Ile Leu Leu Ala Gly Cys Pro Ser Tyr Asp Lys Leu Leu Ser Ala
            180                 185                 190

Lys Asn Lys Asp Tyr Met Ser Ile Ile Arg Met Trp Leu Gly Asp Asp
            195                 200                 205

Val Lys Ser Lys Asp Tyr Ile Val Ala Leu Gln His Pro Val Thr Thr
            210                 215                 220

Asp Ile Lys His Ser Ile Lys Met Phe Glu Leu Thr Leu Asp Ala Leu
225                 230                 235                 240

Ile Ser Phe Asn Lys Arg Thr Leu Val Leu Phe Pro Asn Ile Asp Ala
            245                 250                 255

Gly Ser Lys Glu Met Val Arg Val Met Arg Lys Lys Gly Ile Glu His
            260                 265                 270

His Pro Asn Phe Arg Ala Val Lys His Val Pro Phe Asp Gln Phe Ile
            275                 280                 285

Gln Leu Val Ala His Ala Gly Cys Met Ile Gly Asn Ser Ser Cys Gly
            290                 295                 300

Val Arg Glu Val Gly Ala Phe Gly Thr Pro Val Ile Asn Leu Gly Thr
305                 310                 315                 320

Arg Gln Ile Gly Arg Glu Thr Gly Glu Asn Val Leu His Val Arg Asp
            325                 330                 335

Ala Asp Thr Gln Asp Lys Ile Leu Gln Ala Leu His Leu Gln Phe Gly
            340                 345                 350

Lys Gln Tyr Pro Cys Ser Lys Ile Tyr Gly Asp Gly Asn Ala Val Pro
            355                 360                 365

Arg

<210> SEQ ID NO 6
<211> LENGTH: 364
<212> TYPE: PRT
<213> ORGANISM: Homo sapiens

<400> SEQUENCE: 6

Met Pro Ile Gly Asp Cys Ser Val Ala Ala Lys Pro Arg Lys Gln Leu
1               5                   10                  15

Leu Cys Ser Leu Phe Gln Thr Thr Leu Gly Tyr Arg Ala Arg Ala Ser
            20                  25                  30

Gly Trp Lys Pro Met Val Ile Cys Arg Gly Ser His Ala Phe Lys Asp
            35                  40                  45

Leu Ile Asn Thr Tyr Arg Met Ile Glu Gln Asp Phe Asp Ile Asn
            50                  55                  60

Thr Arg Leu His Thr Ile Val Arg Gly Glu Asp Glu Ala Ala Met Val
65                  70                  75                  80

Glu Ser Val Gly Leu Ala Leu Val Lys Leu Pro Asp Val Leu Asn Arg
            85                  90                  95

Leu Lys Pro Asp Ile Met Ile Val His Gly Asp Arg Phe Asp Ala Leu
            100                 105                 110

Ala Leu Ala Thr Ser Ala Ala Leu Met Asn Ile Arg Ile Leu His Ile
            115                 120                 125

Glu Gly Gly Glu Val Ser Gly Thr Ile Asp Asp Ser Ile Arg His Ala
            130                 135                 140

Ile Thr Lys Leu Ala His Tyr His Val Cys Cys Thr Arg Ser Ala Glu
145                 150                 155                 160

```
Gln His Leu Ile Ser Met Cys Glu Asp His Asp Arg Ile Leu Leu Ala
                165                 170                 175

Gly Cys Pro Ser Tyr Asp Lys Leu Leu Ser Ala Lys Asn Lys Asp Tyr
            180                 185                 190

Met Ser Ile Ile Arg Met Trp Leu Gly Asp Asp Val Lys Ser Lys Asp
            195                 200                 205

Tyr Ile Val Ala Leu Gln His Pro Val Thr Thr Asp Ile Lys His Ser
    210                 215                 220

Ile Lys Met Phe Glu Leu Thr Leu Asp Ala Leu Ile Ser Phe Asn Lys
225                 230                 235                 240

Arg Thr Leu Val Leu Phe Pro Asn Ile Asp Ala Gly Ser Lys Glu Met
                245                 250                 255

Val Arg Val Met Arg Lys Lys Gly Ile Glu His His Pro Asn Phe Arg
            260                 265                 270

Ala Val Lys His Val Pro Phe Asp Gln Phe Ile Gln Leu Val Ala His
        275                 280                 285

Ala Gly Cys Met Ile Gly Asn Ser Ser Cys Gly Val Arg Glu Val Gly
    290                 295                 300

Ala Phe Gly Thr Pro Val Ile Asn Leu Gly Thr Arg Gln Ile Gly Arg
305                 310                 315                 320

Glu Thr Gly Glu Asn Val Leu His Val Arg Asp Ala Asp Thr Gln Asp
                325                 330                 335

Lys Ile Leu Gln Ala Leu His Leu Gln Phe Gly Lys Gln Tyr Pro Cys
            340                 345                 350

Ser Lys Ile Tyr Gly Asp Gly Asn Ala Val Pro Arg
            355                 360

<210> SEQ ID NO 7
<211> LENGTH: 293
<212> TYPE: PRT
<213> ORGANISM: Homo sapiens

<400> SEQUENCE: 7

Met Glu Lys Asn Gly Asn Asn Arg Lys Leu Arg Val Cys Val Ala Thr
1               5                   10                  15

Cys Asn Arg Ala Asp Tyr Ser Lys Leu Ala Pro Ile Met Phe Gly Ile
            20                  25                  30

Lys Thr Glu Pro Glu Phe Phe Glu Leu Asp Val Val Val Leu Gly Ser
        35                  40                  45

His Leu Ile Asp Asp Tyr Gly Asn Thr Tyr Arg Met Ile Glu Gln Asp
    50                  55                  60

Asp Phe Asp Ile Asn Thr Arg Leu His Thr Ile Val Arg Gly Glu Asp
65                  70                  75                  80

Glu Ala Ala Met Val Glu Ser Val Gly Leu Ala Leu Val Lys Leu Pro
                85                  90                  95

Asp Val Leu Asn Arg Leu Lys Pro Asp Ile Met Ile Val His Gly Asp
            100                 105                 110

Arg Phe Asp Ala Leu Ala Leu Ala Thr Ser Ala Ala Leu Met Asn Ile
        115                 120                 125

Arg Asn Pro Ile Leu His Ile Glu Gly Gly Glu Val Ser Gly Thr Ile
    130                 135                 140

Asp Asp Ser Ile Arg His Ala Ile Thr Lys Leu Ala His Tyr His Val
145                 150                 155                 160

Cys Cys Thr Arg Ser Ala Glu Gln His Leu Ile Ser Met Cys Glu Asp
                165                 170                 175
```

His Asp Arg Ile Leu Leu Ala Gly Cys Pro Ser Tyr Asp Lys Leu Leu
            180                 185                 190

Ser Ala Lys Asn Lys Asp Tyr Met Ser Ile Ile Arg Met Trp Leu Gly
            195                 200                 205

Asp Asp Val Asn Pro Lys Ser Lys Asp Tyr Ile Val Ala Leu Gln His
210                 215                 220

Pro Val Thr Thr Asp Ile Lys His Ser Ile Lys Met Phe Glu Leu Thr
225                 230                 235                 240

Leu Asp Ala Leu Ile Ser Phe Asn Lys Arg Thr Leu Val Leu Phe Pro
                245                 250                 255

Asn Ile Asp Ala Gly Ser Lys Glu Met Val Arg Val Met Arg Lys Lys
                260                 265                 270

Gly Ile Glu His His Pro Asn Phe Arg Ala Val Lys His Val Pro Phe
            275                 280                 285

Asp Gln Phe Ile Gln
        290

<210> SEQ ID NO 8
<211> LENGTH: 179
<212> TYPE: PRT
<213> ORGANISM: Homo sapiens

<400> SEQUENCE: 8

Met Ile Glu Gln Asp Asp Phe Asp Ile Asn Thr Arg Leu His Thr Ile
1               5                   10                  15

Val Arg Gly Glu Asp Glu Ala Ala Met Val Glu Ser Val Gly Leu Ala
            20                  25                  30

Leu Val Lys Leu Pro Asp Val Leu Asn Arg Leu Lys Pro Asp Ile Met
        35                  40                  45

Ile Val His Gly Asp Arg Phe Asp Ala Leu Ala Leu Ala Thr Ser Ala
    50                  55                  60

Ala Leu Met Asn Ile Arg Ile Leu His Ile Glu Gly Gly Glu Val Ser
65                  70                  75                  80

Gly Thr Ile Asp Asp Ser Ile Arg His Ala Ile Thr Lys Leu Ala His
                85                  90                  95

Tyr His Val Cys Cys Thr Arg Ser Ala Glu Gln His Leu Ile Ser Met
            100                 105                 110

Cys Glu Asp His Asp Arg Ile Leu Leu Ala Gly Cys Pro Ser Tyr Asp
        115                 120                 125

Lys Leu Leu Ser Ala Lys Asn Lys Asp Tyr Met Ser Ile Ile Arg Met
    130                 135                 140

Trp Leu Gly Ser Lys Glu Met Val Arg Val Met Arg Lys Lys Gly Ile
145                 150                 155                 160

Glu His His Pro Asn Phe Arg Ala Val Lys His Val Pro Phe Asp Gln
                165                 170                 175

Phe Ile Gln

<210> SEQ ID NO 9
<211> LENGTH: 31
<212> TYPE: PRT
<213> ORGANISM: Homo sapiens

<400> SEQUENCE: 9

Thr Leu Val Leu Phe Pro Asn Ile Asp Ala Gly Ser Lys Glu Met Val
1               5                   10                  15

```
Arg Val Met Arg Lys Lys Gly Ile Glu His His Pro Asn Phe Arg
            20                  25                  30

<210> SEQ ID NO 10
<211> LENGTH: 31
<212> TYPE: PRT
<213> ORGANISM: Homo sapiens

<400> SEQUENCE: 10

Thr Leu Val Leu Phe Pro Asn Ile Asp Ala Gly Ser Lys Glu Met Val
1               5                   10                  15

Gln Val Met Arg Lys Lys Gly Ile Glu His His Pro Asn Phe Arg
            20                  25                  30

<210> SEQ ID NO 11
<211> LENGTH: 31
<212> TYPE: PRT
<213> ORGANISM: Homo sapiens

<400> SEQUENCE: 11

Thr Leu Val Leu Phe Pro Asn Ile Asp Ala Gly Ser Lys Glu Met Val
1               5                   10                  15

Trp Val Met Arg Lys Lys Gly Ile Glu His His Pro Asn Phe Arg
            20                  25                  30

<210> SEQ ID NO 12
<211> LENGTH: 31
<212> TYPE: PRT
<213> ORGANISM: Homo sapiens

<400> SEQUENCE: 12

Thr Leu Val Leu Phe Pro Asn Ile Asp Ala Gly Ser Lys Glu Met Val
1               5                   10                  15

Leu Val Met Arg Lys Lys Gly Ile Glu His His Pro Asn Phe Arg
            20                  25                  30

<210> SEQ ID NO 13
<211> LENGTH: 31
<212> TYPE: PRT
<213> ORGANISM: Homo sapiens

<400> SEQUENCE: 13

Thr Leu Val Leu Phe Pro Asn Ile Asp Ala Gly Ser Lys Glu Met Val
1               5                   10                  15

Arg Val Met Gln Lys Lys Gly Ile Glu His His Pro Asn Phe Arg
            20                  25                  30

<210> SEQ ID NO 14
<211> LENGTH: 31
<212> TYPE: PRT
<213> ORGANISM: Homo sapiens

<400> SEQUENCE: 14

Thr Leu Val Leu Phe Pro Asn Ile Asp Ala Gly Ser Lys Glu Met Val
1               5                   10                  15

Arg Val Met Trp Lys Lys Gly Ile Glu His His Pro Asn Phe Arg
            20                  25                  30
```